(12) United States Patent
Johansson et al.

(10) Patent No.: US 6,562,802 B2
(45) Date of Patent: *May 13, 2003

(54) MEDICAL COMPOSITION AND USES THEREOF

(75) Inventors: Benny Johansson, Malmö (SE); Bo Niklasson, Malmö (SE)

(73) Assignee: Noviscens AB, Tygelsjo (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/334,264

(22) Filed: Jun. 16, 1999

(65) Prior Publication Data

US 2002/0128310 A1 Sep. 12, 2002

Related U.S. Application Data

(63) Continuation of application No. PCT/SE97/02126, filed on Dec. 16, 1997.

(30) Foreign Application Priority Data

Dec. 16, 1996 (SE) ............................................. 9604610

(51) Int. Cl.[7] .................. A61K 31/715; A61K 7/42; A01N 43/04
(52) U.S. Cl. .................. 514/55; 514/55; 424/59
(58) Field of Search .................. 514/252, 777, 514/55; 442/121; 428/323; 536/20; 252/180; 210/727

(56) References Cited

U.S. PATENT DOCUMENTS

| | | | |
|---|---|---|---|
| 3,635,818 A | * | 1/1972 | Weckx .................. 210/656 |
| 3,879,376 A | * | 4/1975 | Vanlerberghe et al. |
| 4,031,025 A | * | 6/1977 | Vanlerberghe et al. ...... 252/180 |
| 4,382,864 A | * | 5/1983 | Hashimoto et al. ......... 210/727 |
| 4,822,598 A | * | 4/1989 | Lang et al. |
| 4,929,722 A | * | 5/1990 | Partain, III et al. |
| 4,946,870 A | * | 8/1990 | Partain, III et al. ......... 514/777 |
| 5,000,945 A | * | 3/1991 | Kobayashi et al. |
| 5,140,043 A | * | 8/1992 | Darr et al. |
| 5,348,799 A | * | 9/1994 | Boston ...................... 428/323 |
| 5,368,840 A | * | 11/1994 | Unger |
| 5,576,013 A | * | 11/1996 | Williams et al. |
| 5,698,476 A | * | 12/1997 | Johnson et al. ............. 442/121 |
| 5,733,572 A | * | 3/1998 | Unger et al. |
| 5,744,166 A | * | 4/1998 | Illum |
| 5,854,246 A | * | 12/1998 | Francois et al. ............ 514/252 |
| 6,019,990 A | * | 2/2000 | Remmereit |
| 6,120,751 A | * | 9/2000 | Unger et al. |

FOREIGN PATENT DOCUMENTS

| | | | | |
|---|---|---|---|---|
| EP | 735122 | * | 10/1996 | .......... C09J/133/06 |
| EP | 853941 | * | 7/1998 | ............ A61K/7/50 |
| WO | 96/09636 | | 6/1992 | |

OTHER PUBLICATIONS

Muzzarelli, Natural chelating polymer, pp. 164–174, 222–227 and 228–245.*
Grawkrodger et al, The prevention of nickel contact dermatitis . . . , Contanct Dermatitis, 1995, vol. 32, pp. 257–265.*
"*The Prevention of nickel contact dermatitis A review of the use of binding agents and barrier creams*," authored by D.J. Gawkrodger, et al., published in Contact Dermatitis, vol. 32, pp 257–265, 1995.
STN International, File CAPLUS, CAPLUS accession no. 128:16378, Valenta C. et al., "Chitosan–EDTA Conjugate: A Novel Polymer For Topical Used Gels," *Farm. Vestn.* (Ljubljana) (1997), 48 (Pos. Stev.), 354–355.
STN International, File CAPLUS, CAPLUS accession no. 123:265799, Baba, Yoshimi et al., "Skin Preparations Containing N–Acylated Chitosan," JP, A2, 07196468, dated Aug. 1, 1995, Heisei.
STN International, File CAPLUS, CAPLUS accession no. 1989:141226, Yanagida, Takeshi et al., "Skin and Hair Preparations Containing Taurines and Water–Soluble Chitin Derivatives," JP, A2, 63277608, dated Nov. 15, 1988.
STN International, Derwent Information Ltd., WPIDS accession no. 96–246872, Nisshin Flour Milling Co. et al., "Agents for Skin External Use–Comprise Alpha–Tocopheryl Retinoate in Water–in–Oil Emulsion," JP, A, 08099834, dated Apr. 16, 1996; and.

\* cited by examiner

*Primary Examiner*—William R. A. Jarvis
*Assistant Examiner*—Vickie Kim
(74) *Attorney, Agent, or Firm*—Smith, Gambrell & Russell

(57) ABSTRACT

A composition is described, which comprises a cationic, hydrophilic, amine containing cationic derivatives of native chitosan; bound to an anionic scavenger substance, which is either (a) selected from the group consisting of anionic ethylene amine compounds, tetraazacycloalkane-N,N,N,N-tetraacetic acids; and polymer derivatives of porphyrines, or, (b) in the case of use in an UV radiation absorbing formulation, an antiviral, antifungal or anti-inflammatory formulation, an endogenous compound wherein cationic derivatives of native chitosan are not covalently bound to DTPA or EDTA; the amount of EDTA exceeds 0.5 wight percent; and taurine and taurine derivatives are not present.

18 Claims, 11 Drawing Sheets

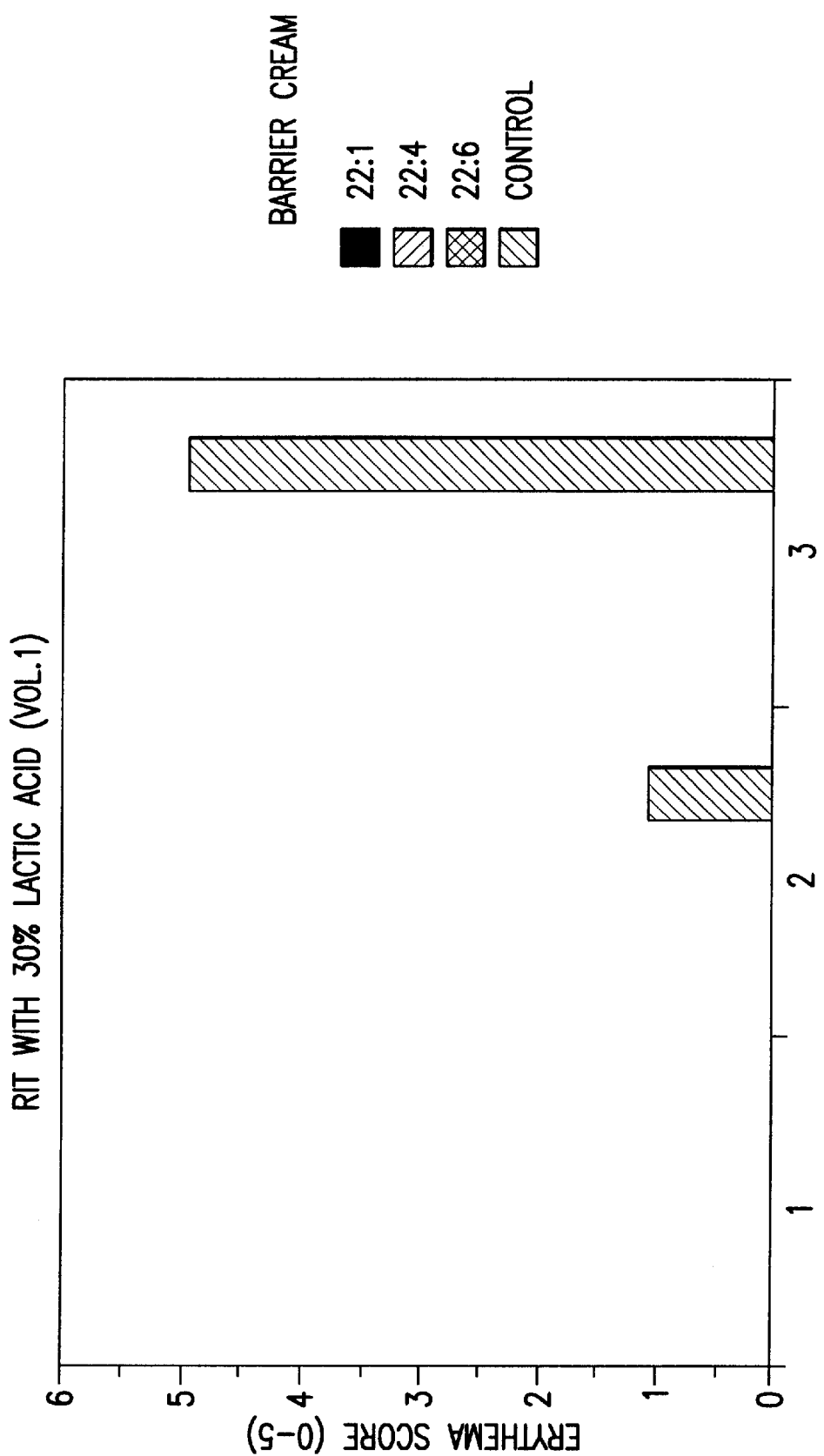

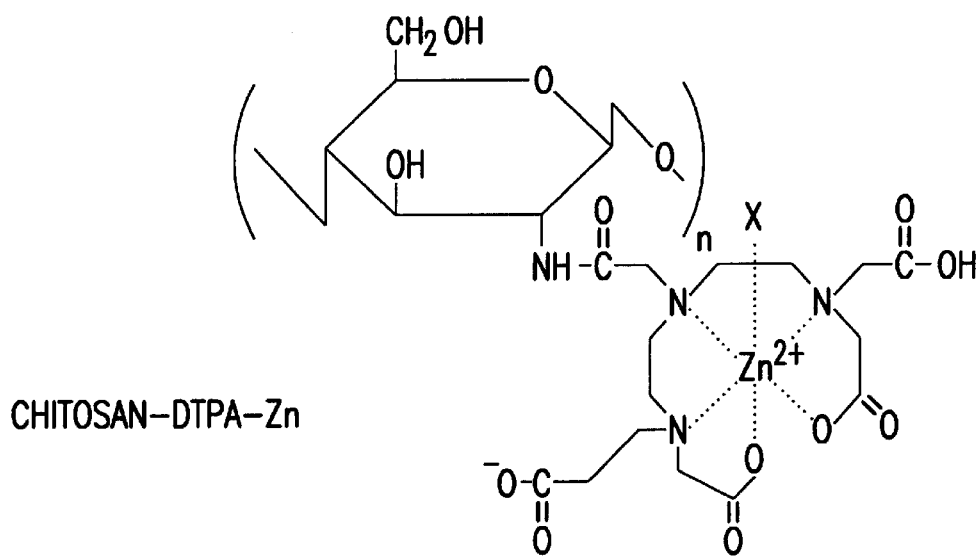
CHITOSAN-DTPA-Zn
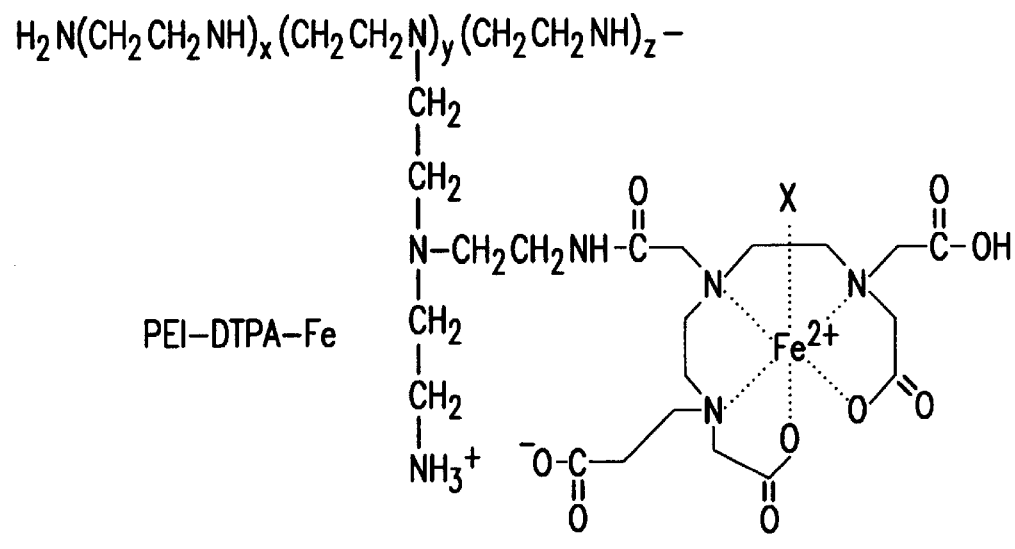
PEI-DTPA-Fe
METHOXY-PEG-AMIDE DERIVATIVES 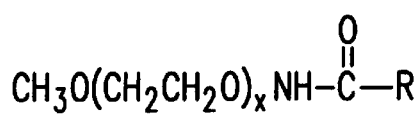
R = SUBSTITUENT CONTAINING A CARBOXY GROUP
FIG.9

MEDICAL COMPOSITION AND USES THEREOF

RELATED APPLICATION DATA

This application is a continuation of PCT/SE97/02126 filed Dec. 16, 1997, which application is relied upon and entirely incorporated herein by reference. Additionally, this application claims priority benefits based on Swedish Appln. No. 9604610-7, filed in Sweden on Dec. 16, 1996, which application also is relied upon and entirely incorporated herein by reference.

TECHNICAL FIELD OF THE INVENTION

The present invention relates to a medical composition and use thereof for the manufacture of a topical barrier formulation, an UV-radiation absorbing formulation, or an antiviral, antifungal, or antiinflammatory formulation.

Since the first epidemiological data on allergic contact dermatitis reported in the thirties, nickel has been the most frequent allergen in women. The primary site for sensitization has changed, from suspenders to metal buttons in jeans to pierced ear lobes. Sensitization may also occur from occupational contact with objects like electrical assembly, cuff links, locksmith tools, dental equipment, scissors, knitting equipment, chemical reagents etc.

In the following, the focus is on the severe condition of hand eczema, but obviously, eczema on other sites like the stomach caused by nickel containing jeans buttons or on ear lobes caused by contact with earrings is a big problem.

The sources of primary sensitization resulting in hand eczema are either occupational or environmental. Occupations include platers, metal workers, cashiers, hairdressers or office workers. Environmental primary sensitization include housewives, environment and hobbies with nickel exposure. In patients already sensitized to nickel, the risk of acquiring hand eczema is far greater, especially when the skin is damaged. In many cases a multifactorial situation, including nickel exposure, exposure to irritants, atopic constitution and other factors plays a role. Investigations in the USA, Finland and Denmark have shown that the number of nickel sensitive women in the general population approximates 10% (1,2,3).

However, a higher frequency of nickel allergy (15–18%) is found in the age groups where hand eczema commonly develops (4). When hand dermatitis develops in the nickel sensitized subjects, the condition becomes a definite threat to the individual's working ability. In a study from Denmark it was shown that nickel hand eczema is the most common skin disease which leads to permanent disability (5). This results in huge costs for the social welfare system and in personal suffering for the patients. In another Danish study (6) based on a questionnaire sent to a stratified sample (2500) of the female population, it was concluded that 43% of the nickel sensitive subjects reported hand eczema. The study also demonstrated that women who were nickel sensitive ran an increased risk of developing hand eczema compared to non-nickel-sensitive women. Also, those who already had a hand eczema were more likely to develop nickel allergy. As pointed out earlier, the risk of developing nickel allergy increases when the skin is injured as is the case in e.g. irritant contact dermatitis caused by exposure to irritants like detergents in working or home environment. A study investigating the bioavailability of nickel from consumer products was made (7) and the provocation threshold in nickel sensitive patients varied from 0.47 µg to 5.2 mg.

The current method for treating nickel dermatitis is basically to treat the acute eczema with corticosteroid creams and advise the patients to avoid nickel containing objects, which is obviously a difficult task. Another method that has been used experimentally is to administer nickel chelating agents like disulfiram (8). Although some improvement of the patients' eczema was achieved, side effects in the form of flare-up reactions and hepatotoxicity was noted. Triethylenetetramine has been used in the same manner, however without resulting in any significant improvement (9). In addition, reports of teratogenicity in rats by triethylenetetramine indicated a limited value of the method.

A recent review of the use of binding agents and barrier creams (10) showed that the most effective nickel chelating substance is 3% clioquinol applied topically in a cream in combination with 1% hydrocortisone. The method used was patch testing with cream-coated 20 pence coins in 26 nickel-sensitive subjects (11).

However, clioquinol toxicity has been found in dogs treated daily with 5 g of a 3% preparation for a month, and there may be a risk of toxicity in infants and children from its topical use. Also, clioquinol is a known contact allergen and is present in the European Standard Series for the detection of contact hypersensitivity. It is therefore considered unsuitable for the purpose of preventing nickel dermatitis. A certain effect, expressed as decreased patch test reactivity, was found for EDTA in combination with 1% hydrocortisone, where only 40% of the subjects showed reduced nickel patch test reactivity (11). The purpose of using an active barrier cream is to prevent nickel from coming into contact with the epidermis of the skin, and to avoid use of corticosteroid topical treatment on the inflammation of the skin. The negative effects of prolonged use of corticosteroids is well known.

In another study (12), where pretreatment of a cream containing 10% $Na_2H_2EDTA$ was used, somewhat better results were achieved in reducing patch test reactivity (76%). The maximum challenge concentration in this study was however only 1% of nickel sulfate, compared to 5% which is normally used in patch testing. A patch test study (13) in 21 nickel sensitive individuals where nickel discs were applied on top of Carbopol barrier gels containing 10% $CaNa_2EDTA$ showed that the discs without pretreatment gave a positive reaction in 11 out of the 21 subjects. All of the subjects showed a positive reaction to 5% nickel sulfate. Since only 11 out of 21 subjects reacted to the discs, it seems that the release of nickel ions from the discs was insufficient for inducing a positive reaction. The 11 subjects positive to the challenge by the disc did not react when the disc was applied on top of the barrier gel. A blank gel without $CaNa_2EDTA$ also showed a reduction in sensitivity where 3 out of 11 showed a positive reaction on challenge to the disc and 7 patients showed a reduced reaction when treated with the vehicle.

From an experiment in vitro it was shown that the gels caused an increase in the release of nickel ions from the alloys. This is considered as an unwanted effect since it counteracts the barrier effect of the formulation.

Studies using tin complexes with EDTA, cyclohexane-1, 2-diaminetetraacetic acid (CDTA) and diethylenetriaminepentaacetic acid showed only poor results in chelating nickel, chromium and cobalt (14). The fact that none of the above mentioned creams have resulted in any commercially used product further underlines the need for developing an effective active nickel barrier cream.

Cobalt allergy is often associated with nickel allergy because the metals are often associated with each other. A positive test to cobalt occurs 20 times more frequently in those allergic to nickel than in those not allergic. The frequency of cobalt patch test positive patients is around 7%, and of-these around 50% are isolated reactions. However cobalt also occurs isolated in various products such as printing inks, paints, polyester resins, electroplating, wet alkaline clay in pottery, porcelain dyes, animal feeds.

Trivalent chromium penetrates the skin very poorly, binding to proteins on the surface of the skin, whereas hexavalent chromium penetrates the skin easily but binds poorly to proteins on the surface of the skin. It is thought that hexavalent chromium penetrates the epidermis and is then reduced by enzymes to the trivalent form which combines with proteins to form the allergenic compound.

The true frequency of patch test positive patients to chromate is probably in the range of 2–4%. The most common cause of chromate allergy is contact with cement. Other sources are from chrome-tanned leather, antirust paint, timber preservatives, matches with chromate in the match head, coolants and machine oil and many other sources.

Dermatitis from chromate sensitivity is normally quite severe and has a poor prognosis.

Allergic reactions on the skin and oral mucosa induced by gold, i.e. the $Au^+$ and $Au^{3+}$ ions, have also been encountered and is a problem for several persons, especially in dental treatment.

Oral hyposensitization in nickel allergy with repeated oral doses of nickel sulfate has been studied (15). The degree of contact sensitivity was found to decrease especially when higher doses of nickel sulfate was administered (5 mg/week). However, the majority of patients had a flare-up of their dermatitis and it was concluded that high oral doses are inconvenient to the patients. Other models have been evaluated against Rhus allergens where a moderate decrease in Rhus sensitivity was found after oral or intramuscular administration of Rhus allergens (16). Another hyposensitization study was made on North American healthy subjects sensitized to the poison ivy and poison oak allergen urushiol (17). Increasing oral doses of urushiol were given over a protracted period and resulted in a lowered degree of patch test reactivity. Side effects in the form of rashes and anal pruritus were the main complications.

From the above discussion it is evident that there is no current effective treatment or product that does not cause undesired side effects, that can be used effectively for the prevention of nickel or related metal dermatitis or dermatitis caused by organic allergens found in materials such as Rhus or Poison ivy or Poison oak. The latter allergen containing plants cause wide-spread dermatitis in many subjects in especially North America.

This underlines the importance of developing products that actively can facilitate the prevention of contact dermatitis from metals or organic allergens either through an active barrier function via strong chelating properties or by induction of tolerance in sensitized individuals. Further, there is an urgent need for a barrier formulation that protects from irritation caused by various agents such as detergents, alkaline and acidic products and solvents, combined with an active metal-chelating agent that prevents from metal sensitization. This is due to the fact that irritant dermatitis often coexists with allergic contact dermatitis caused by metals, and that these two conditions aggravate the symptoms of the patients. A model of testing the efficacy of general barrier creams (without addition of any active chelating agent) against irritants has been developed (18). Sodium lauryl sulfate (SLS), sodium hydroxide (NaOH), lactic acid and toluene were used as irritants. Partial protection was shown for two commercial creams to SLS, NaOH and lactic acid, but not to toluene. Generally, "non-active" barrier creams against irritation might in fact enhance the penetration of allergens such as nickel through the epidermis, although some are marketed as being effective also in the protection against allergens. This fact further emphasizes the importance of a combined formulation including an active chelating agent in a barrier cream against irritants.

Further, currently skin diseases such as photoaging, skin cancer, sunburn, drug phototoxicity, hyperpigmentation, UV-induced immunosuppression and diseases aggravated by sunlight are treated by means of protecting the skin against UV A and UV B radiation. Protecting agents are various UV A and UV B absorbing sunscreens such as benzophenones, dibenzoylmethane, methylanthranilate, Padimate-O or physical sunscreens such as zinc oxide or titanium oxide. Also, tretionin, pigment inducing agents (5-MOP), antioxidants and free radical scavengers are used. These protective agents however give an inadequate protection and several agents are also contact and photo-contact sensitizers. An effective UV A and UV B protecting topical formulation with low toxicity and allergenicity would be a valuable addition to the present agents in the protection against diseases induced by UV A and UV B radiation.

There is also a constant strive in the development and need for better and less toxic antivirus agents for the therapy of viral infections. A major advance was the development of Acyclovir that exerts selectivity in the inhibition of virus replication at low concentrations. Although this agent is used in various dosages and delivery routes against Herpes simplex viruses 1 and 2 and varicella zoster virus it has its limitations due to poor absorbtion from the gastrointestinal tract, weak action against varicella zoster virus and is inactive against cytomegalo virus as well as showing drug resistance pattern. An active topical formulation with low toxicity and allergenicity would be a valuable addition to the present agents in the treatment of viral infections.

Further, imidazol derivatives such as ketoconazole, econazole, miconazole and clotrimazole as well as terbinafine are currently used as topical treatment against fungal diseases induced by dermatophytes and pityriasis versicolor causing skin and nail infections as well as candida also causing infection on the mucosa. More severe infections are treated with oral agents such as griseofulvin, ketoconazole, terbinafine, itraconazole and fluconazole. Undesired effects in the form of hepatotoxicity, altered liver function, gastrointestinal side effects and skin reactions have been noted for the oral agents and contact allergic reactions for the imidazol derivatives have been showed. An active topical formulation with low toxicity and allergenicity would be a valuable addition to the present agents in the treatment of fungal infections.

BACKGROUND ART

Some prior art formulations contain chitosan or chitosan derivatives in combination with dietylene triamine penta acetic acid (DTPA).

Nihon Mediphysics has, in JP 08-0112579, proposed the use of topical agents for radiotherapy of cancer. The formulation is based on a hydrophilic gel forming polymer, e.g. chitosan, covalently bound to a radioactive metal ion via a complexing agent. The-radioactive metal ion is specified to be the indium (III) isotope. This patent application is clear-cut limited to the topical treatment of cancer in combination with radiation therapy. In contrast, the products according to the present invention are not intended for use in medical radiotherapeutic treatments. The purpose is inter alia protection against development of contact dermatitis, or pharmaceutical treatment thereof. Further, in one embodiment of the present invention the formulation is based on a soluble anionic metal chelating agent, e.g. DTPA, and not on DTPA covalently bound to the polymer. The anionic DTPA interacts with a cationic hydrophilic polymer, e.g. chitosan, and not with uncharged derivatives thereof.

Catalysts & Chemical Ind Co has in another Japanese patent specification, JP 07-112128, proposed the use of adsorption agents for the separation of nickel, cobalt, and aluminum from chemical engineering or chemical processes. This publication also refers to a covalent derivative of chitosan in reaction with either ethylenediaminetetraacetic acid (EDTA) or DTPA. This application is neither intended for, nor applicable for medical use of any kind, only for the separation of metal ions in chemical processes.

Antioxidant skin cosmetics containing ascorbyl esters, thiols and completing agents, e.g. DTPA, have been proposed in FR 2 610 626 to protect especially skin lipids from oxidation. The purpose of that invention is the protection against chemical interaction with oxygen and oxygen species, where the complex forming agents stabilize e.g. endogenous ferric ions from participation in the oxidative skin reactions, and are certainly not intended to chelate exogenous allergenic metal ions.

In WO 92/09636, a method is proposed for protecting the skin and minimizing skin irritation by the topical use of protective compositions. This publication deals with a physical barrier formulation, composed of compounds with film-forming protective properties. The composition is intended to protect the skin from contact with irritant allergenic or toxic agents. However, the formulation is deficient in active protection of low or high molecular weight compounds. The protection is intended to be achieved only by the use of derivatives of chitosan, or in combination with anionic polymers, but not by native chitosan. The combination of the different types of polymers is supposed to optimize the film-forming properties of the composition. However, in clinical studies in humans with contact dermatitis caused by poison oak/ivy, the protective effect exerted by the compositions tested were not significant. The results indicate that the barrier effect based on physical mechanisms is insufficient, i.e. the allergenic compounds can still be transferred across the skin barrier and provoke the allergic inflammatory reaction.

The inhibitory effect of various topical chelating agents on nickel-contact dermatitis has been reviewed recently (Cont. Derm. 32: 257–265: 1995) and studied previously after treatment with barrier ointments containing EDTA (J. Am. Acad. Dermatol. 30: 560–565: 1994; Cont. Derm. 26: 197. 1992. and Cont. Derm. 11: 311–314: 1984). The results from clinical studies indicate that EDTA significantly blocks the allergenic effects of nickel in some nickel sensitive patients. However, this complexing agent is not sufficiently effective in all patients. The chelating effect of tin complexes with e.g. DTPA has also been studied, and the compounds were found ineffective as nickel chelators. The unique combination of DTPA or analogous metal ion complexing agents with cationic, hydrophilic amino-containing polymers, which constitutes an accomplished effective active nickel barrier formulation, has not been described previously.

SUMMARY OF THE INVENTION

The object of the invention is to eliminate or alleviate the above-mentioned problems associated with different dermatological skin and mucosa related disorders induced by allergens, skin irritating agents, ultraviolet radiation, viruses, fungi, and inflammatory inducing factors.

This object is achieved according to the present invention with a medical composition which is defined in the characterising part of the independent claims. Preferred embodiments of the present invention are also defined in the dependent claims.

BRIEF DESCRIPTION OF THE DRAWINGS

The present invention and different embodiments thereof will be described more in detail below with reference to the accompanying drawings, in which:

FIG. 6 shows the efficacy of skin barrier creams after irritation tests with lactic acid, FIG. 9 shows the structure of DTPA covalently linked to chitosan and PEI forming $Zn^{2+}$ and $Fe^{2+}$ metal complexes, respectively, and methoxy-PEG attached to any substance containing a carboxylic group.

DETAILED DESCRIPTION OF PREFERRED EMBODIMENTS OF THE PRESENT INVENTION

Figure 1:
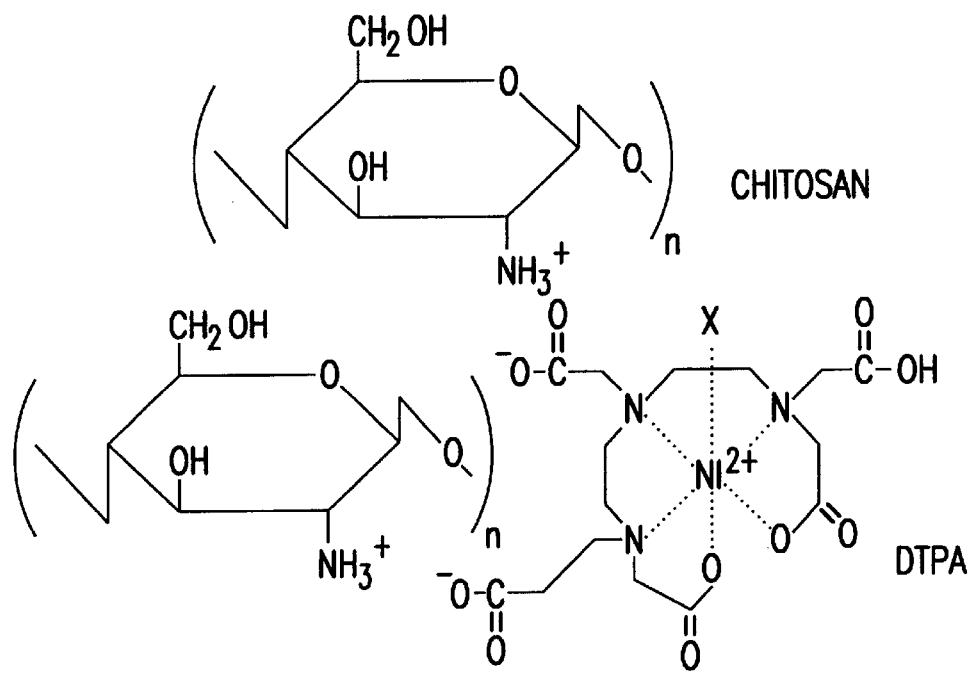
FIG. 1 shows the structure of a composition according to the present invention based on chitosan and DTPA to which nickel has been complexed.
Figure 2:
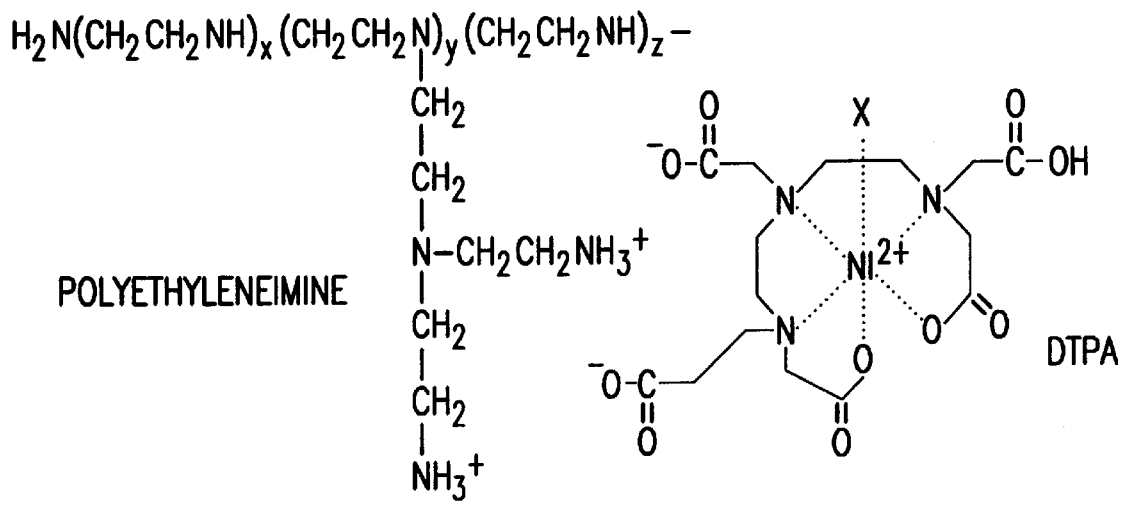
FIG. 2 shows the structure of a composition according to the present invention based on PEI and DTPA to which nickel has been complexed.
Figure 3A:
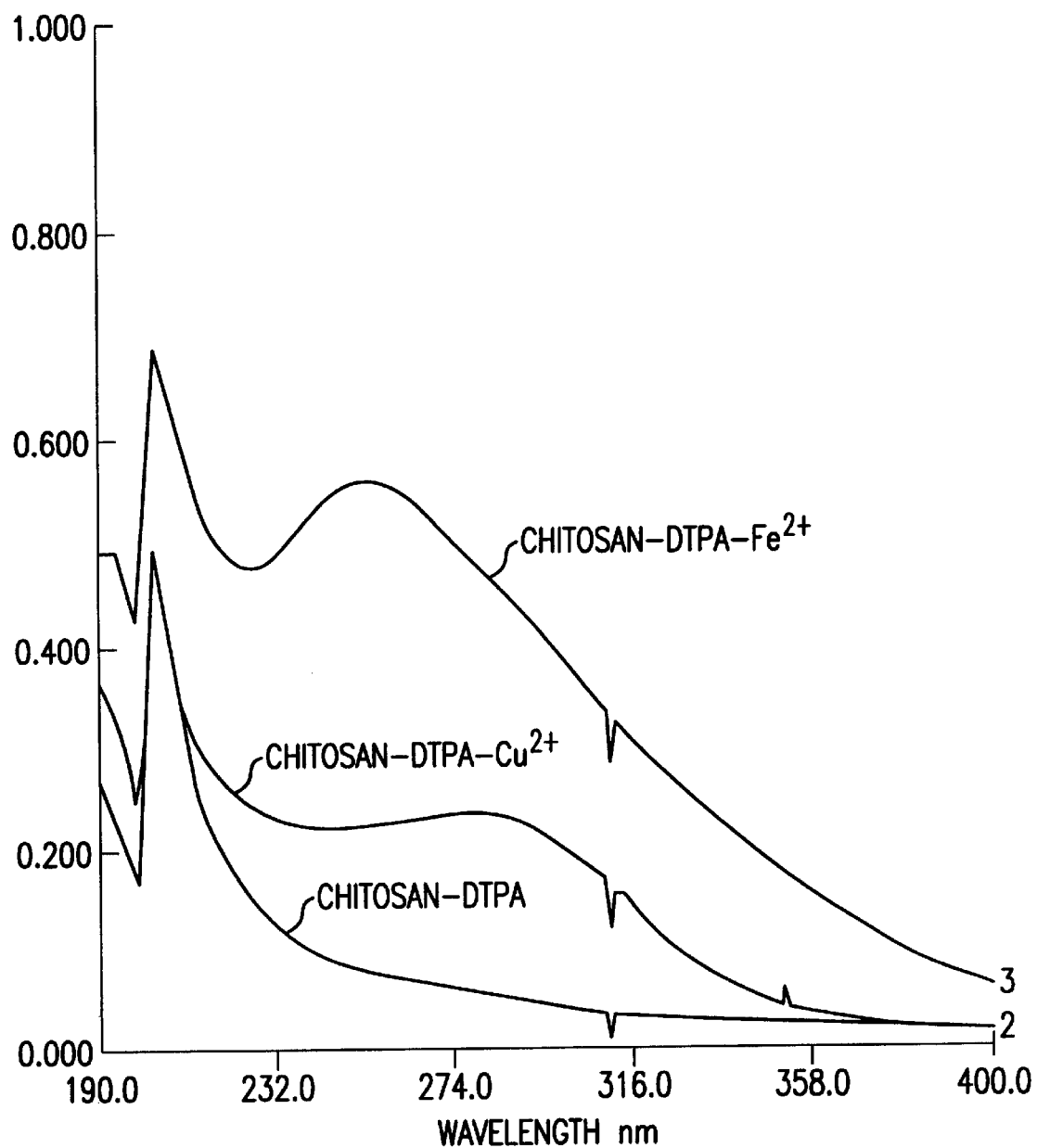
FIG. 3A shows UV absorption spectra of chitosan-DTPA-$Fe^{2+}$ and chitosan-DTPA-$Cu^{2+}$ complexes.
Figure 3B:
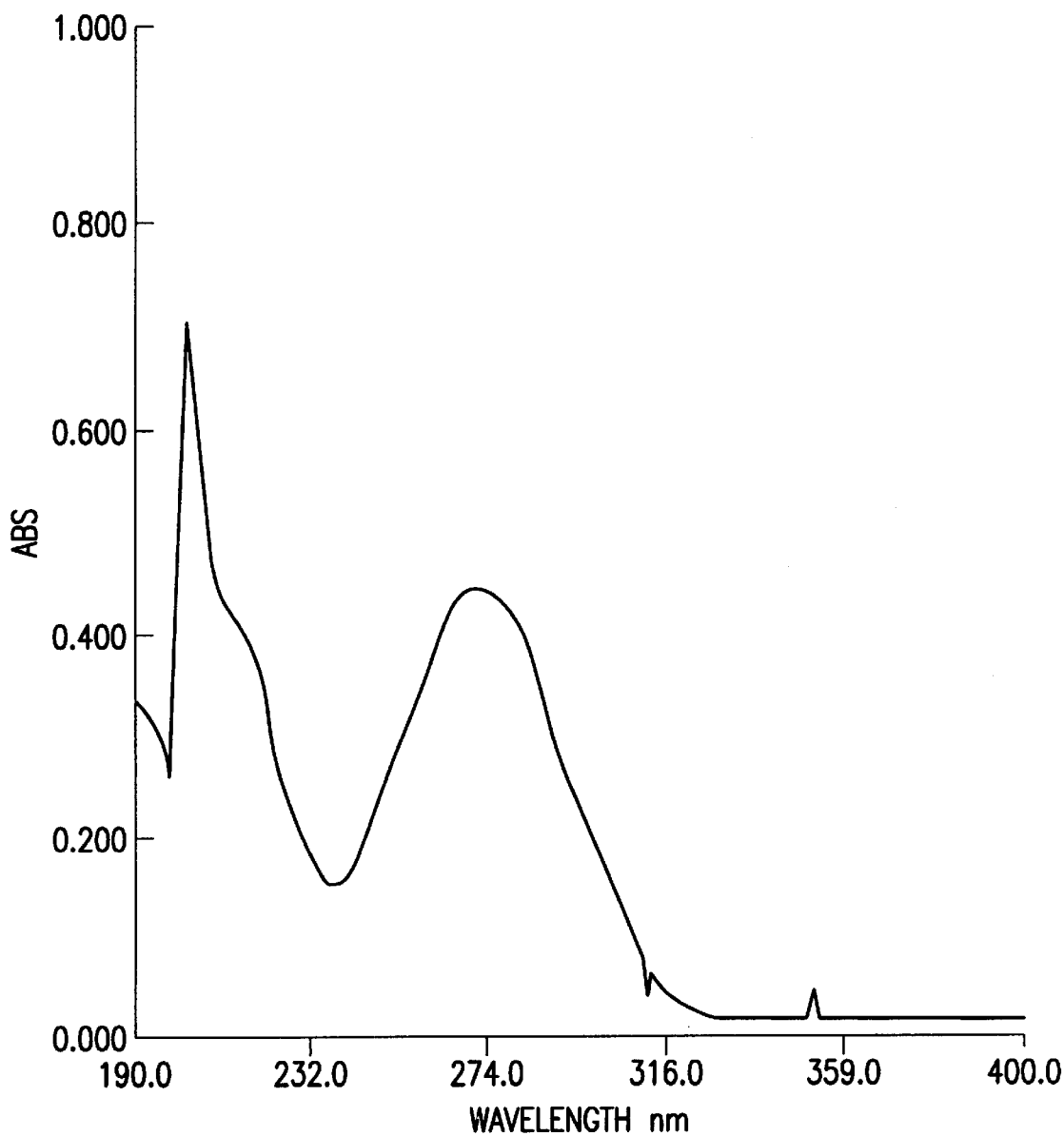
FIG. 3B shows UV absorption spectra of polyethylene-N-PABA.

In one embodiment of the present invention the medical composition is used in a protective and/or a therapeutic topical barrier formulation for the treatment of dermatological disorders induced by allergens and skin irritating agents, or is used for the manufacture of such a formulation.

In another embodiment of the present invention the medical composition is used in a protective UV radiation absorbing formulation for the prevention and/or treatment of dermatological disorders induced by UV radiation, or is used for the manufacture of such a formulation.

In still another embodiment of the present invention the medical composition is used in a protective and/or therapeutic antiviral, antifungal and/or antiinflammatory formulation for the treatment of dermatological disorders, induced by viruses, fungi and/or inflammatory conditions, or is used for the manufacture of such a formulation.

The composition according to the present invention is new, except from the particular embodiment when native chitosan or derivatives thereof is/are covalently bound to EDTA or DTPA.

The common inventive concept of the different embodiments of the present invention is that a cationic, hydrophilic polymer and an anionic scavenger substance, bound together by either ionic or covalent bonds, have a unique capacity to scavenge or capture body-foreign substances, such as organic and inorganic allergens and skin or mucosa irritating agents, as well as UV radiation, when applied to the skin and mucosa of human beings and animals. Alternatively, the cationic, hydrophilic polymer has the ability to separately capture body foreign substances.

With the term "medical composition" used in the description and claims is meant a composition useful in the art and science of the diagnosis, prophylaxis, protection against and treatment of diseases and the maintainance of health. This term encompasses the preparations according to the present invention for external application to the body.

With the term "cationic, hydrophilic amino-containing polymer" used in the description and claims is meant a polymer which is film-forming, nontoxic, non-penetrating and biocompatible with skin when administered as a polymeric carrier of various sequestrating functional substances.

With the term "anionic scavenger substance" used in the description and claims is meant an optionally complexing soluble endogenous or exogenous substance with bi-functional chemical functionalities, in such a way that the anionic entity of the molecule is whether retained by ionic forces by the hydrophilic backbone structure of the cationic polymer or as an interaction between the polymer and the cutaneous or mucosal proteins or covalently bound to the polymer, while the scavenging entity of the molecule is operating separately.

With the term "antiallergenic" used in the description and claims is meant an endogenous or exogenous low molecular weight substance or a polymer containing one or more functional groups with high chemical reactivity for various organic allergens or high metal ion chelating avidity for metal allergens, and which obliterate the allergenicity of the allergens.

With the term "exogenous substance" used in the description and claims is referred to as a substance developed or originating outside the organism.

With the term "endogenous substance" used in the description and claims is meant a substance produced or originating within the organism, or arising from causes within the organism.

With the term "animals" used in the description and claims is meant domestic, sports animals or animals bred for production of animal meat.

With the term "skin-irritating agents" used in the description and claims is meant substances that cause an irritant reaction or acute irritant contact dermatitis, defined as a non-allergic inflammatory reaction of the skin or mucosa.

With the term "homolog" used in the description and claims is meant a series of compounds, each of which is formed from the one before it by the addition of a constant element or a constant group of elements.

TOPICAL BARRIER FORMULATION

When used in a protective and/or therapeutic topical barrier formulation for the treatment of dermatological disorders induced by allergens and skin irritating agents according to one embodiment of the present invention, the anionic scavenger substance is an antiallergenic compound or a scavenger of skin irritating agents, ionically bound to the cationic, hydrophilic amine containing polymer. The topical barrier formulation also comprises one or more skin-protective lipophilic substances and is preferably applied on human and animal skin or mucosa in the form of a cream, an oil, a gel or an ointment.

The cationic, hydrophilic amine containing polymer is non-toxic and skin-non-penetrating and forms a gel or a film on the skin. The polymer is chosen from the group consisting of native chitosan and derivatives thereof having a cationic character, e.g. chitosan carbamic acid, chitosan chloride, 6-0-carboxymethylchitosan, 6-0-di-hydroxypropylchitosan, 6-0-hydroxyethylchitosan, 6-0-sulphatechitosan, N-sulphatechitosan, and N-carboxy-butylchitosan; polyethylene compounds, e.g. PEI (polyethylene imine), aminated PEG (polyethylene glycol), MPEG (monomethoxy substituted PEG), phosphate and carbamate derivates thereof, or a polysaccharide chosen from the group consisting of DEAE-4, and polyornitine.

The anionic antiallergenic substance is the active principle in the topical barrier formulation and is comprised of chemically active, low or high molecular compounds of both exogenous and endogenous origin. The antiallergenic exogenous substances are chosen from the group consisting of DTPA (diethylenediaminepentaacetic acid) and calcium and sodium salts thereof, EDTA (ethylenediaminetetraacetic acid), triethylenetriamine-hexaacetic acid, ethylenediaminetetra(methylphosphoric acid), DTPMPA (diethylenetriaminepenta(metylphosphoric acid) and homologs thereof, tetraethylenetetraaminehexa-acetic acid, tetraazacykloalkane-N,N,N,N-tetraacetic acids, preferably DOTA, TRITA and TETA; polymerderivatives of porphyrines, preferably tetra(4-carboxyphenyl)-porphyrine. These substances have the ability to chelate different allergenic metals, particularly $Ni^{2+}$, $Cr^{3+}$, $Cr^{6+}$, $Co^{2+}$, $Au^+$ and $Au^{3+}$. The antiallergenic endogenous substance is chosen from the group consisting of taurine, hypotaurine, cysteine, cysteamine, panteteine, N-acetyl-cysteine and certain anionic polyamine metabolites.

The antiallergenic substance abolish the allergenicity of the allergens. The topical barrier formulation protects the skin and mucosa from contact with inter alia contact sensitizing metals, various organic allergens, including allergenic proteins, and skin irritating agents. The antiallergenic substances inactivate the reactivity of the allergenic compounds in the volume space of a hydrophilic polymer gel. A preferred topical barrier formulation comprises native chitosan as the polymer, ionically bound to DTPA as anionic scavenger substance for the protective and/or therapeutic treatment of contact dermatitis induced by nickel ions.

In the following, the topical barrier formulation and the chemical and biological mechanisms thereof are presented in detail.

The cationic, hydrophilic amine containing polymer has at least two features which make it superior as a protector in combination with active anionic antiallergenic substances, towards contact with, inter alia, contact sensitizing allergens. Previous studies have shown that cationic polymers, e.g. chitosan, poly-L-lysine and polyethyleneimine, promote adhesion to various biological tissues and surfaces, although the mechanisms are poorly understood. Inorganic cations e.g. $Na^+$ and $Mg^{2+}$, inhibit chitosan-mediated adhesion to cell membranes, presumably by interfering with electrostatic interactions responsible for adsorption of the polymer to anionic charged surface proteins in cell membranes. In the presence of these inorganic cations or the polymeric (poly) cations, the microenvironment of the cell membrane surface becomes highly hydrophobic, probably due to the loss of surface electronegativity from negatively charged carboxylate protein residues. This phenomenon renders an adhesive interaction of a hydrogel of the cationic polymer with proteins of not only the skin, but also the mucosa of human tissue. The cationic, hydrophilic amine containing polymer forms a stationary hydrogel, which is strongly retarded by interchange ionic forces between the gel and skin proteins. Within the normal pH-range (5.0–7.0) of human skin, native chitosan forms a hydro-gelatinous film with a cationic charge at pH values below the pKa value of 6.3 of chitosan. The anionic anti-allergenic substances, i.e. exogenous compounds, e.g. metal chelators, or endogenous compounds, are preferably water soluble and have active functional groups directed towards reaction with allergenic compounds. Further, they are readily dissolved in the water volume space of the hydrogel. In addition, due to their negative charge in the pH range of human skin, these anionic compounds are mostly retained by the cationic charge of the polymer, and therefore exert their innocuous function towards allergens in the back-bone structure of the hydrogel. It is imperative that the pH of the formulation is kept below the pKa value of chitosan to sustain the cationic charge of the polymer. If not, the polymer looses its retaining qualities towards the anionic substances. At an optimal pH value, the allergen is captured by active chemical forces on the surface of the skin, and its transport and penetration through the epidermial barrier is thereby inhibited.

As stated above, the cationic, hydrophilic amine-contaning polymer is, inter alia, chosen from the group consisting of native chitosan, chitosan carbamic acid, chitosan chloride, polyethylene imine, aminated polyethylene glycol (PEG) and MPEG. Of particular interest is native chitosan having a molecular weight range of 1–1,000 kilodaltons (kd), preferably 50–250 kilodaltons (kd). Native chitosan is composed of partly deacetylated chitin, which is extracted from shrimp and crab shells, and transformed into chitosan to obtain a water-soluble product. Chitosan is a linear biopolymer, which consists of two monosaccharides, N-acetyl-D-glucoseamine and D-glucoseamine, linked together by glycosidic bonds. The relative amount of the two monosaccharides may vary, giving products of different degrees of deacetylation. Commercial chitosans have a degree of deacetylation of 75–95%. Preferably, the deacetylation degree of the native chitosan may vary between 0 and 100%, most preferably between 40 and 95%. Native chitosan and the other polymers mentioned form viscous solutions or hydro-gels. The viscosity depends on both size (degree of polymerisation) and conformation of the polymer. The cosmetic applicability of topical dermatological formulations is highly dependent on the tactile perception by the consumer or patient. Tactile perception involves a contact and movement of fingertips across the skin surface in contact with the formulation, and the relative movement between the two skin surfaces is affected or restricted by friction. The experience of this friction plays an important role in the objective evaluation of consumer-perceptible skin attributes. The tactile feeling must be pleasant, not slippery or too hard. Increasing the molecular weight of native chitosan to above approximately 250 kd, increases the apparent viscosity exponentially and influences the tactile perception, giving a less acceptable formulation. Therefore, it is important that the formulation contain native chitosan at a molecular weight of less than 250 kd. However, in salt solutions the viscosity of chitosan is lower, and consequently more freely soluble than in non-salt solutions. By the proper use of chitosan salts, which are non-irritating and acceptable to the skin, together with essential lipids and humectants in blends, a formulation with high consumer preference may be obtained. Most preferably, the composition is formulated as a gel or a cream, based on oil/water or water/oil emulsions. Suitable non-active salts of chitosan are acetates, citrate, formate, hydrogen carbonate, fumarate, glycinate, glycolates, hydrochloride, lactate, malate, malonates, oxalate, palmitate, phosphate, pyruvate, stearate, succinate, or salts of various amino acids. During preparation, the pH of the solution must be kept below 8.0, because most chitosan salts are insoluble above this pH value. Chitosan is also compatible with alcohols and acetone at concentrations up to 50% with sustained viscosity without any precipitation.

Another useful branched polymer biocompatible with the skin is PEI (see FIG. 2), in which preferably about 25% of the amines are primary amines, 50% are secondary, and 25% are tertiary. PEI is cationic at physiological pH values, and is most suitable as an anionic retainer in the molecular weight range of 1–200 kd, preferably about 50 kd. PEI is freely soluble both in water and various organic solvents with a moderate viscosity. The primary amino groups are more reactive than secondary amines, and most reactive towards various allergenic functional groups in a suitable environment. Many allergenic chemicals have electrophilic properties and are able to react with various endogenous nucleophiles to form covalent bonds. Considering the human tissues from a chemical point of view, especially nucleic acids and proteins contain many electron-rich groups (nitrogen, phosphorus, oxygen and sulphur). The most nucleophilic targets are lysine and cysteine, but also amino acids with hetero-atoms, like histidine, methionine and tyrosine, react with electrophiles, inducing allergenic effects. The most reactive electrophilic chemical groups found frequently in allergens, can be divided into three groups. The first group reacts by nucleophilic substitution on a saturated centre, and includes alkylhalides and epoxides. The second group reacts by nuclophilic substitution on an un-saturated centre, which includes aromatic halides, lactones, lactames or esters. The third type reacts by nucleophilic addition, considering carbonyl derivatives, e.g. aldehydes and ketones and $\alpha/\beta$-unsaturated systems, like quinones. Because of the high reactivity of particularly the primary amines of PEI in reaction with various allergenic electrophilic functional groups, these allergens might be rapidly extinguished directly by PEI, if brought together. Alternatively, at the pH values of human skin, the reactivity of PEI becomes lower (pKa is about 9.8 for primary amines and around 8 for secondary amines), and allergens are therefore more likely retained by ionic forces similar to those of native chitosan.

Besides, the direct scavenging effect towards electrophilic allergens of e.g. PEI, activated aminopoly-saccharides of, e.g. chitosan, could also be used as an adduct-forming agent of allergens. At the pH range of human skin, usually below the pKa value of chitosan, the protonated amino group of chitosan is stabilized, and therefore almost non-reactive towards most allergenic electrophiles. However, by activation of the amino group of native chitosan, using either of two biological activation agents, carbon dioxide or sodium hypochlorite, the reactivity of the amino group is extensively increased. Carbamoylation of amino groups in peptides, proteins and certain metabolites of drugs has been identified as a general and functionally important activating phenomenon in biological chemical reactions. Formation in vivo of stable carbamic acid compounds depends on pH and $PCO_2$ of the intracellular environment of the cell. During oxidative stress, myeloperoxidase of neutrophiles (a leukocyte) catalyzes the formation of hypochlorous acid (HOCl) from hydrogen peroxide and chloride anions.

Hypochlorous acid is a potent oxidizing and chlorinating agent with biocidal properties. It can directly chlorinate several biological significant molecules, forming secondary chlorinating agents with detoxifying, scavenging and regulatory properties. Both activating processes discussed must therefore be considered as novel chemical reaction promoting methods with high biological significance and with high acceptance from an environmental point of view.

Native chitosan is carbamoylated in a water solution by gaseous carbon dioxide, bubbling through the solution at ambient temperature. The pH of the solution is continuously monitored, and adjusted to a pH in the range of 5.5–6.5 during the reaction, by the addition of sodium hydroxide. The reaction is normally completed within 3–4 hours. Carbamoylated chitosan forms a compound with high stability at physiological pH in water solutions. Chlorination of chitosan is performed in a water solution, by careful addition of a less (to avoid cross-linking) than stoichiometrical amount (1:10–1:500) of sodium hypochlorite, in relation to the amount of amino groups in chitosan. The reaction is rapid and is completed within 5 minutes at ambient temperature. Both carbamoylated and chlorinated chitosan derivatives are compounds which, besides having high water-solubility, also are freely soluble in alcohols, acetone and various organic solvents, and in mixtures thereof. The reaction yield of the two activation processes can be followed by determination of the amount of free amino groups, before and after activation.

Besides the forth-mentioned dermatological application of chitosan and activated chitosans, preliminary results from clinical pilot studies after topical administration also indicate that activated chitosans, particularly carbamoylated chitosan, disrupt the active phase in Herpes simplex infections, accelerate the healing process of psoriatic skin lesions and promote increased cutaneous permeability, which may increase topically applied drug absorbtion. These observations, which will be illustrated in detail below, are in accordance with previous skin healing properties of chitosan products. Examples include healing effects on burns, wound healing, tissue regeneration (reconstruction of paradental tissue), bacteriostatic, antiviral and antimycotic effects and immunostimulating activity. The increased cutaneous permability obtained by chitosan carbamic acid, probably also promotes cutaneous absorption of various aeroallergens, and therefore might be used in patch test diagnosis of atopic dermatitis.

As stated above, the scavenger substance, i.e., anionic antiallergenic substance according to the presently described embodiment of the invention has the ability to chelate or complex $Ni^{2+}$, $Cr^{3+}$, $Cr^{6+}$, $Co^{2+}$, $Au^+$, and $Au^{3+}$ ions. DTPA and calcium and sodium salts thereof are the most preferred antiallergenic substances, i.e. as anionic chelators of allergenic metal ions. DTPA is a pentacarboxylic acid of diethylenetriamine with pKa values in the range of 2.0–10.3. Due to its pentacarboxylic structure, allergenic metal ions, especially $Ni^{2+}$, $Cr^{3+}$, $Cr^{6+}$, $Co^{2+}$, $Au^+$, and $Au^{3+}$, are chelated by very high stability constants in the range of pKs 19–20 (25° C., I=0.15). Only two of the five carboxylic acid groups are extensively involved in the formation of the complex with the metal cation, while at least two of the other three carboxy groups with pKa values below 6.3 are less involved, and are therefore more prone to interact with the polycationic polymer (see FIG. 1). This phenomenon probably explains the retardation of the DTPA metal ion complex within the volume-space of the hydrogel. The binding capacity of acidic metal chelators depends on the pKa values of the acids, and is therefore highly influenced by the pH of surrounding environment. Decreasing the pH below the critical pKa value(s) results in a reduced or complete loss in binding capacity.

Solubilized in the cationic polymer hydrogel, particularily chitosan, the binding capacity of DTPA is fairly stable, due to the native buffering qualities of chitosan. Other anionic metal chelating substances which can be used in combination with the polycationic hydrogel are e.g. EDTA, triethylenetriaminehexaacetic acid and homologs thereof, ethylenediaminetetra (methylphosphoric acid), diethylenetriaminepenta(methylphosphoric acid) (DTPMPA) and homologs thereof, and phosphate and carbamate derivatives of the above-mentioned polymers. The toxicity of both DTPA and DTPMPA is extremely low, with acute and subacute toxicities of less than 6 g/kg in mice, rats and rabbits. DTPA is characterized in European Pharmacopoeia as a component in sterile solutions, containing e.g. Technetium 99 or Indium 111 for complex formation, intended for injections in humans in connection with radiopharmaceutical diagnosis.

Besides the abolishment of allergenic metal ions by complex formation with water soluble metal chelators, retarded in the hydrogel, other allergenic compounds of various organic origin can be captured by small anionic antiallergenic molecules, in a way similar to contact sensitizing metals. Preferentially, endogenous antioxidants, antiallergens or other scavenging molecules, e.g. taurine, hypotaurine (and their chlorinated or carbamoylated derivatives), cysteamine, cysteine, N-acetylcysteine (and acidic metabolites of polyamines, e.g. γ-amino-butyric acid, hypusine, putreanine and spermic acid), are water-soluble non-toxic substances, which readily associate to the polycationic hydrogel (see FIG. 1). All these substances have non-protonated acidic groups at the pH range of human skin, and are therefore anionic and retained by the polymer. The scavenging groups are either primary amines or thiols, the two most endogenous-like nucleophiles with high adduct forming efficacy. Thiols are prone to autooxidation in solutions at a pH above 7.0, and therefore it is imperative to keep pH in the formulation below this critical point, to avoid oxidation of the thiols. Preferentially, the formulation is also stabilized by the addition of a non-allergenic antioxidant.

The lipophilic substances included in the topical barrier formulation render it a creamy character, and consist of e.g. stearic acids or derivatives thereof. These substances penetrate the lipophilic areas of the upper layer of the stratum corneum, creates a network with endogenous cell membrane lipids, and stabilize the lamellar lipid phase between the keratinized cells of the epidermal horny layer.

UV RADIATION ABSORBING FORMULATION

When the medical composition according to the present invention is used in an UV radiation absorbing formulation for the protective treatment of dermatological disorders induced by UV radiation, the cationic, hydrophilic amine containing polymer is covalently bound to the anionic scavenger substance. The cationic, hydrophilic amine containing polymer is chosen from the same group as defined above for the topical barrier formulation. The anionic scavenger substance is also chosen from the same group as defined above for the topical barrier formulation, except from EDTA or homologs thereof.

In the UV radiation absorbing formulation ions chosen from the group consisting of $Cu^{2+}$, $Fe^{2+}$, $Fe^{3+}$, and $Eu^{3+}$ and/or combinations thereof, are chelated to the anionic scavenger substance.

Optionally, the polymer is covalently bound to the anionic scavenger substance via a an immobilisible spacer, preferably p-aminobenzoic acid or 3,3'-4,4'-benzophenontetracarboxylic acid.

In a preferred embodiment of the UV radiation absorbing composition, the cationic, hydrophilic amine containing polymer is PEI, covalently bound to DTPA as anionic scavenging substance. The UV radiation absorbing formulation and the biological mechanisms thereof will now be described in detail below.

Commercially available UV-filters used for absorption of UV radiation are based on water or oil soluble substances. The UV radiation active compounds are freely absorbed by the epidermis and are subject to metabolism in e.g. keratinocytes, which is a potential source of formation of allergenic metabolites of the non-allergenic parent compounds. Therefore, it is imperative to maintain the UV radiation sequestrating ability above the surface of epidermis, by covalently immobilized UV quenching structures. The present UV radiation absorbing formulation containing the active ingredients is to be applied directly on the skin, where the active compounds are supposed to sequestrate harmful UV radiation. There are two most distinguishing qualities of the composition having protective activity against UV radiation in which the anionic scavenger substance is covalently attached to the cationic, hydrophilic amine containing polymer. First, there is an apparent sequestration of UV radiation before it reaches the skin surface. Normal sunscreen compounds have been-reported to protect against erythema and inflammation, but recent studies have revealed a minimal protection against local and systemic immunosuppression. Evidence more and more indicate that UV-induced immunosuppression contributes to the development of skin cancers, cutaneous photoaging and various cutaneous inflammatory disorders in humans. Studies on mice have shown that UV radiation destroys both enzymatic and non-enzymatic antioxidant defenses in epidermis and dermis. Reactive oxygen species (ROS) are generated both by physiological oxidative metabolism and by external causes, of which UV light may be the most important in our daily life. The antioxidative systems protect against the damage mediated by ROS. Further, antioxidants interact in a complex fashion by optimizing redox status, or the concentrations of redox active compounds in one part of a comprehensive network, which affects the entire system. Destruction or weakening of the antioxidant defenses of the epidermis and dermis by ROS support the free-radical hypotheses of UV induced skin damage. Thus there is a possibility of widespread protein disfunction, which leaves the skin open to further oxidative stress from any source. These results propose that the composition of the formulation of commercially available sunscreens is insufficiently optimized for complete sequestration of particularly UV B and UV A radiation. This observation also indicates that the penetration ability and vicinity between the UV absorbers and the three skin layers, enables at least partial impignation of solar radiation to penetrate into varying depths of the skin. The depth to which the radiation penetrates into the skin depends on the wavelength of the penetrating light. The penetration depth increases as the wavelength of the radiation increases. Therefore, it is imperative to quench and transform radiation of wavelengths harmful to the skin into radiation quanta of less harmful energy, prior to its impignation with the skin.

Experimental results have shown that the immunoprotective capacity of sunscreens correlates mainly with the absorption-spectra of the sequestrating compounds. Substances with a broad UV absorption spectrum have the highest immunoprotective capacity. Most organic sunscreens are highly efficient UV absorbers in the UV B range (290–320 nm) and the lower UV A range (320–340 nm). Inorganic compounds, such as zink oxide, titanium oxide and silicates are highly efficient broad spectrum absorbers (290–400 nm) or reflectants of radiation, and thereby the most effective immunoprotective sunscreens. The disadvantage of these substances is that the skin assumes a mask-like appearance. For this reason in particular, these substances are normally not used as sun-screen agents, apart from reinforcing UV filters. That is why there is an apparent need for new sunscreen agents with sequestration qualities which strengthen the normal protective function of the skin against UV radiation.

Secondly, the rigid attachment of the active UV absorber, i.e. the anionic scavenger substance, e.g. the chelator, to the backbone structure of the polymer, abolishes penetration of the absorber through the epidermis, and thereby also its transportation to the metabolizing cell compartments. Apparently, with this novel concept, there is no risk for metabolic formation of allergenic or toxic metabolites.

The UV absorbers covalently bound to the polymer may be composed according to two different concepts. Polyabsorbers can either be produced by e.g. DTPA, the preferred anionic scavanger substance, covalently linked to the polymer, e.g. native chitosan, or, e.g. PEI or modified PEG. The anionic scavenger substance, e.g. DTPA or its homologs can also be covalently bound via an UV-absorbing spacer to the polymer (Charles, S. H. et al. Attachment of fluorescent metal chelates to macromolecules using bifunctional chelating agents. Biochem. Biophys. Res. Commun. 75, 149–155, 1977). The UV absorbing spacer amplifies the absorbing capacity of the polymeric metal complex. DTPA, covalently immobilized to the polymers, has for example UV absorbing qualities in the UV C range, i.e. below 230 nm. Formation of metal complexes with biocompatible metal ions, e.g. $Cu^{2+}$, $Fe^{2+}$, $Fe^{3+}$, and $Eu^{3+}$, further expand the UV absorption range, including both UV B and UV C radiation (see FIG. 3). According to the second concept, commercially available UV filters, with sustained UV absorbtion capabilities after immobilization to the polymer, can also be utilized in light-screening formulations.

In the preferred embodiment DTPA is covalently attached with high efficiency to any cationic, hydrophilic amino-containing polymer by the method of Krejcarek & Tucker (Biochem. Biophys. Res. Commun. 77, 1977, 581–585). DTPA is subject to the formation of a mixed carboxycarbonic anhydride of DTPA in reaction with isobutylchloroformate (IBCF) in the presence of the strong base, triethylamine (5 times molar excess in relation to DTPA). After dissolution of DTPA in water and base, the mixture was lyophilized, and redissolved in formamide. IBCF was added in a 1:1 molar ratio in relation to DTPA, with gentle stirring, and the temperature was maintained at 4° C. The reaction was completed within 30–45 min. The polymer, e.g. native chitosan or PEI, was dissolved in water, and the mixed anhydride of DTPA was added. The pH was maintained at approximately 6.5–7.0 by addition of pyridine. The reaction was completed within 24 hours as shown by the ceasing formation of carbon dioxide. The mixture was precipitated by the addition of ethanol. The precipitate was washed with ethanol and acetone and dried at ambient temperature. The dry product of native chitosan is not soluble in salt-free water, but is so in various salt solutions, e.g. physiological saline. The DTPA derivative of PEI is directly soluble in water, as well as in various organic solvents. The maximal metal ion binding capacity of the DTPA polymers of e.g. chitosan and PEI was calculated from binding studies with $Ni^{2+}$ ions, and estimated to be 0,65 mmol/g and 1.61 mmol/g polymer, respectively. The result indicates that approximately 27% of the available primary amines in chitosan and 55% of those in PEI, are occupied by DTPA, which means that the cationic character is maintained after the derivatization procedure of the polymers.

Modified PEG, in the form of monomethoxy substituted PEG (MPEG), is also useful as a polymeric carrier of UV sequestrating groups. MPEG was modified according to the following method. 22.9 ml (4 mmol) of sodium hypochlorite was added to 10 g (2.0 mmol) of monomethoxy PEG (5 kd) under vigorous mixing. The chlorination was completed within 24 hours. Chlorinated MPEG was aminated by addition of 12 ml (185 mmol) 29% (w/w) ammonium hydroxide solution in water. The reaction mixture was heated at 50° C. for 48 hours. Unreacted ammonium hydroxide was evaporated. The residue was washed repeatedly with ethanol and then dried at ambient temperature. The MPEG-amine can be derivatized according to the methods discussed previously.

Coupling of the UV-absorbing spacer between the polymer and e.g. DTPA or its analogs, can be performed according to the method described by Leung & Meares (Biochem. Biophys. Res. Commun. 75, 1977, 149–155).

The metal ion complexes of the polymers are readily formed in a water solution of the polymer, by the addition of a stoichiometrical amount of a suitable metal salt, also dissolved in water. The salt-free polymetal chelator is preferably obtained by precipitation in ethanol as discussed in the text above, or by continuous dialysis against Milli Q purified water for 24 hours. The water is removed by lyophilization.

Attachment of commercially available UV absorbers or other non-toxic substances, with UV radiation absorbing capacity, to the above-mentioned polymers can be, although necessarily, performed by, e.g. mixed anhydride formation in reaction with IBCF and a carboxylic acid group or derivative of the UV absorbing compound. Examples of water soluble UV absorbers are p-methoxysalicylic acid, p-aminobenzoic acid, gallic acid, cinnamic acid, p-methoxycinnamic acid, o-hydroxybenzoic acid, benzimidazoleic acid, dihydroxybenzoic acids, 2-benzoylbenzoic acid, 3,3'-4,4'-benzophenontetracarboxylic acid and retinoic acid. UV filters containing hydroxyl or amino groups are readily converted to the corresponding acid derivative by reaction with an equimolar amount of acetic anhydride or succinic anhydride in pyridine. Most of these products are more hydrophobic than the corresponding DTPA derivatives and therefore more suitable for oil-based formulations.

The UV absorbing characteristics, determined as the sunscreen index, according to Kumler, is given in Table 1, of some poly-absorbents of UV radiation. All values are within the range of defined commercial UV absorbers.

TABLE 1

Polyabsorbents of UV radiation

|  | Sunscreen index |
|---|---|
| p-aminobenzoic acid (reference) | 7.4 |
| Chitosan-DTPA-$Cu^{2+}$ | 4.5 |
| Chitosan-DTPA-$Fe^{2+}$ | 8.0 |
| Polyethylene-N-p-aminobenzoic acid | 6.2 |

The concentration of the cationic, hydrophilic amino-containing polymer, used in the preparation of formulations intended for fabrication of the skin protective compositions of this invention, i.e. both the topical barrier formulation and the UV radiation absorbing formulation, range from 0.05 up to 15 weight percent, preferably from 0.5 to 5.0% based on the total weight of the composition. The polymer is preferently dissolved in physiological saline. When DTPA is used as anionic scavenger substance, it could be added either as the pentasodium salt or dicalcium/trisodium salt. The active anionic scavenger substance are added at a concentration ranging from 0.5 up to 20 weight percent, preferably 5 to 15%. The protective formulation is preferably composed of either a gel or water/oil (cream) or oil/water (ointment) emulsion.

In the form of a gel, the composition is preferably based on native chitosan in combination with the active compound, further humectants, e.g. urea, L-lactic acid, glycerine, propylene glycol, glycerol and sorbitol.

These humectant compounds are added at a concentration ranging from 0.5 up to 10 weight percent. The addition of humectants facilitate an interaction and adhesion between negatively charged surface proteins in the extra-cellular space of the horny layer of the skin, and the cationic polymer, which also influences the frictional resistance on the skin surface and the tactile perception of the formulation by the consumer. Auxiliary gellants, such as carboxymethyl cellulose and gellan gum may also be added in a concentration ranging from 0.5 up to 5%, based on weight, to increase the stability of the gel.

Cream-based formulations are based on compositions, which besides the creamy character, also increases the physical and chemical resistance towards irritating, corroding, dissolving and intoxicating agents. The hydrophobic ingredients of the composition penetrate the lipophilic areas of the upper layer of stratum corneum, and creates a network with endogenous cell membrane lipids. It stabilizes the lamellar lipid phase between the keratinized cells of the epidermal horny layer, like the bricks of a wall embedded and hold together by mortar. In addition, the hydrogel formed by e.g. chitosan or chitosan derivatives constitutes a buffering layer on the surface of the skin. The chitosan network offers a high neutralizing capacity both against acids and alkaline compounds and solutions, and thereby protects the epidermis from harmful corrosive agents.

The hydrophobic components such as stearic acid and paraffine; emulsifiers such as cetylstearylalcohol, surfactants such as polyoxyethylene-2-stearylether; emollients such as dimethylpolysiloxan and cetylalcohol, can be added at concentrations ranging from 0.5 up to 20%, based on weight. Other ingredients like authorized preservatives and fragrances may also be added in different amounts to make up a stable composition.

An example of a suitable design of the topical active barrier formulation may preferably be composed in the form of a cream having the following basic ingredients and proportions.

(I)

| Ingredients | Composition (% (w/w)) | |
|---|---|---|
| | Range | Preferred |
| Cetylstearylalcohol | 0.5–20 | (6–10) |
| Polyoxyethylene-2-sterarylether | 0.5–20 | (1–5) |
| Paraffine liquid | 0.5–20 | (0.5–5) |
| Glycerol | 0.5–10 | (0.5–5) |
| Urea | 0.0–10 | (0.0–5 |
| DTPA (Na/Ca salt)** | 0.5–20 | (5–15) |
| Chitosan (hydrochloride)* | 0.05–15 | (0.5–5) |
| Physiological saline | 20–60 | (30–50) |

Other suitable forms may be comprised of the following two compositions.

| Ingredients | Composition (% (w/w)) | |
|---|---|---|
| | Range | Preferred |
| (II) | | |
| DTPA (Na/Ca salt)** | 0.5–20 | (5–15) |
| Chitosan (hydrochloride)* | 0.05–15 | (0.5–5) |
| Cetylstearylalcohol | 0.5–20 | (3–10) |
| Glycerol | 0.5–10 | (0.5–5) |
| Paraffin liquid | 0.5–10 | (1.0–10) |
| Polyoxythylene(2)stearylether (Brij ® 72) | 0.5–10 | (0.5–5) |
| Polyoxythylene(21)stearyl-ether (Brij ® 721) | 0.5–10 | (0.5–5) |
| Polyoxypropylene(15)stearyl-alcohol | 0.5–15 | (0.5–10) |
| Sodiumhydroxide | 0.5–10 | (0.5–5) |
| Aqua, purified | 20–80 | (40–80) |
| (III) | | |
| DTPA (Na/Ca salt)** | 0.5–20 | (5–15) |
| Chitosan (hydrochloride) | 0.5–15 | (0.5–5) |
| Glycerol | 0.5–10 | (0.5–5) |
| Paraffin liquid | 0.5–15 | (1.0–10) |
| Isohexadekan (Arlamol HD) | 0.5–15 | (1.0–10) |
| Magnesiumchloride hexahydrate | 0.5–10 | (1.0–10) |
| POP-POE Glycerolsorbitan-hydroxystearate (Arlacel 780) | 0.5–15 | (1.0–10) |
| Sodium hydroxide | 0.5–10 | (0.5–5) |
| Aqua, purified | 20–80 | (40–80) |

An example of a suitable design of the topical active barrier formulation may preferently be composed in the form of a gel having the following basic ingredients and proportions.

| Ingredients | Composition (% (w/w)) | |
|---|---|---|
| | Range | Preferred |
| (IV) | | |
| Glycerol | 0.5–10 | (0.5–5) |
| Urea | 0.0–10 | (0.0–5) |
| DTPA (Na/Ca salt)** | 0.5–20 | (5–15) |
| Chitosan (hydrochloride)* | 0.05–15 | (0.5–5) |
| Carboxymethyl cellulose | 0.05–5 | (0.5–2) |
| Physiological saline | 60–85 | (65–75) |

*Chitosan can be replaced by its derivatives, or other polymers and their derivatives.
**DTPA can be excluded or replaced by antiallergens according to the patent.

Antiviral, Antifungal and Antiinflammatory Formulations

A number of spin-off treatment effects have also been found through various modifications of the basic active principles of the medical composition according to the present invention. These additional medical indications cover prevention and/or treatment of dermatologic skin disorders, such as herpes infections, fungal infections and psoriasis.

When used in a therapeutic antiviral, antifungal or anti-inflammatory formulation for the treatment of dermatological disorders induced by viruses, fungi, and inflammatory conditions, according to one embodiment of the present invention, the cationic, hydrophilic amine containing polymer is activated chitosan, or is ionically bound to endogenous, thiol-containing compounds chosen from the group consisting of taurine, hypotaurine or their activated derivatives, cysteine, cysteamine, panteteine, N-acetylcysteine, and acidic metabolites of polyamines. The cationic, hydrophilic amine containing polymer may also be chosen from the same group as for the topical barrier formulation and UV radiation absorbing formulation.

Since several degenerative skin disorders, e.g. viral infections such as Herpes simplex infections, fungal diseases such as Tinea and Candida infections, and psoriatric skin disorders, have been inadequately treated by topical and systemic pharmacological medications, it has been attractive to investigate the therapeutic benefits of particularly a topically applied activated chitosan derivative on various immunodeficiency-dependent skin disorders. The proposed skin-active polymer has no systemic bioavailability, and the therapeutic benefits is probably induced on the local lymphoid tissue of the surface-active immune system, e.g. in the epidermis and dermis. The key factor is the penetration ability of the cationic polymer, through the horny layer of the epidermis. Stimulated immunocompetent cells migrate readily through skin tissue and are partly stationary in the epidermis. Apparently, the polymer must penetrate the horny layer, but necessarily not migrate into the epidermis or further on to other skin layers to reach contact with these cells, probably along the less rigid epidermal route that goes between the keratinocyte clusters. This part of the epidermis is more flexible and permits transcutaneous water loss and probably also transport of various components, which are needed in the chemical defenses of the skin. Apparently, this route also facilitates transport in the opposite direction of compounds applied on the skin surface. It is therefore proposed that polycationic polymers or their derivatives, particularity the carbamic acid derivative, which are able to improve transnasal absorption of peptides, e.g. insulin and calcitonin (Illium, L., Farraj, N. F. Davis, S. S. Pharm. Res. 11, 1994, 1186–1189; Aspden, T. J., Illum, L. and Skagrud. Eur. J. Pharm. Sci. 4, 1996, 23–31.), by a proposed mucosal adhering and transient widening of tight junctions in membranes, may use the between keratinocyte clusters route, to make contact and interaction with immunocompetent cells.

In accordance with e.g. DTPA, any carboxylic acid containing low molecular weight compound, can be attached to the amino-containing polymer by the method of Krejcarek and Tucker (for details see part 1 of this invention). Substances with hydroxylic and amino functional groups can be converted to a carboxylic acid derivative in reaction with iodo or chloroacetic acid according to the method of Grud (Methods in Enzymology XI, pp. 532–541). The formed carboxylic acid derivative can be attached to the polymer by the method discussed. Alternatively, the acid derivative of the polymer, e.g. the phosphate or carbamic acid derivatives, can be formed directly in reaction with phosphorus pentoxide or carbon dioxide according to common synthetic methods. The polymeric metal complexes with $Zn^{2+}$ ions are readily obtained as discussed above. Native chitosan has preferential binding qualities for especially $Zn^{2+}$ ions and might be an alternative to the synthesized polymeric metal chelators.

The antiviral formulation according to the present invention is particularity useful for the treatment of infections induced by Herpes simplex.

The antifungal formulation according to the present invention is particularity useful for the treatment of skin diseases induced by Tinea and Candida dermatomycoses.

The antiinflammatory formulation according to the present invention is particularity useful for the treatment of chronical psoriasis.

The antiviral, antifungal and antiinflammatory formulations may also comprise substantially the same additional components as the topical barrier formulation. Further, the proportions of the polymer and the anionic scavenger substance in these formulations are substantially the same as in the topical barrier formulation.

Medical Formulations

The topical barrier formulation used according to the present invention is preferably dermally administered on the skin in the form of a cream, an ointment, a gel, or an oil.

The UV A and B radiation absorbing formulation used according to the present invention is preferably dermally administered on the skin and the lips in the form of a cream, an ointment, a gel, a liniment, a lotion, an oil, or a lip preparation.

The antiviral, antifungal and antiinflammatory formulation used according to the present invention is preferably administered dermally, ophthalmically, on the lips, or in the mucous membrane-anal region and the vulvo-vaginal region, in the form of a cream, an ointment, a gel, a liniment, a lotion, an oil, an ophthalmic preparation, a suppositorium, or a lip preparation.

The amounts of active ingredients and the specific dose level for any individual to be treated will depend upon a variety of factors including the particular use of the formulation and the route of administration.

EXAMPLES

The different embodiments of the present invention will now be described in detail in the non-limiting examples below. The amounts stated throughout in the examples are all given as percent by weight, unless otherwise stated.

Example 1

A Cream-Based Active Barrier Formulation Intended for Protection Against Nickel Exposition 7.5 g DTPA (sodium/calcium salt) and 2.0 g urea are dissolved in 29.25 ml physiological saline (pH 6.5). 1.25 g chitosan hydrochloride (Mw: approximately 180 kd) are dissolved in the physiological saline solution and mixed until the polymer is completely dissolved. 6 g cetylstearylalcohol, 2.5 g polyoxyethylene-2-steraryl-ether, 1 g glycerol and 0.5 g paraffine liquid are mixed and melted together in a water bath at 70–75° C. The DTPA/gel solution is heated to 60° C. and mixed with the hydrophobic ingredients at 60° C. until a creamy consistency appears. A preservative may also be added, but is not necessary because DTPA itself shows preservative activity.

In the case of preparation of a gel, 1 gram of carboxymethyl cellulose may also be added together with chitosan to the water solution to make up a stable gel formulation. During dissolution, the solution my be heated at 60° C. until the polmers are completely dissolved. At cooling a stable gel forms spontaneously.

In order to investigate the protective barrier effect of the above mentioned active barrier formulations, 21 supposed nickel sensitized patients were provoked by a nickel burden patch-test, applied on the skin of the back of the patients.

The patients were pretreated with the two active barrier formulations and one blank cream formulation without addition of DTPA. 0.5 ml of each formulation was applied on equally 45.5 cm² skin areas on the backs of the patients. One control area without pretreatment were also used. Nickel sulphate (20 μl) was applied in plastic IQ chambers (Chemotechnique Diagnostics, Malmö, Sweden) on the four skin areas at five different concentrations, 0.08, 0.25, 0.8, 2.5 and 8% (w/w), dissolved in Milli Q purified water. The five concentrations were applied at random within each skin area. The patients were then exposed for 48 hours to the patch test. The result was evaluated by visual scoring, based on a scale from 0 to 6, by two experienced dermatologists, at 72 hours and 4 and 7 days after the start of exposure. Scoring scale: 0 no reaction; 1=weak positive reaction involving erythema, infiltration (+); 2=more intense weak positive reaction involving erythema, infiltration, possibly papules +; 3=weak to strong positive reaction involving erythema, infiltration, papules +(+); 4=strong positive reaction involving erythema, infiltration, papules, vesicles ++; 5=strong to extreme positive reaction involving erythema, infiltration, papules, vesicles and some coalescing vesicles ++(+); 6=extreme positive reaction involving intense erythema and infiltration, and coalescing vesicles +++.

Figure 4:
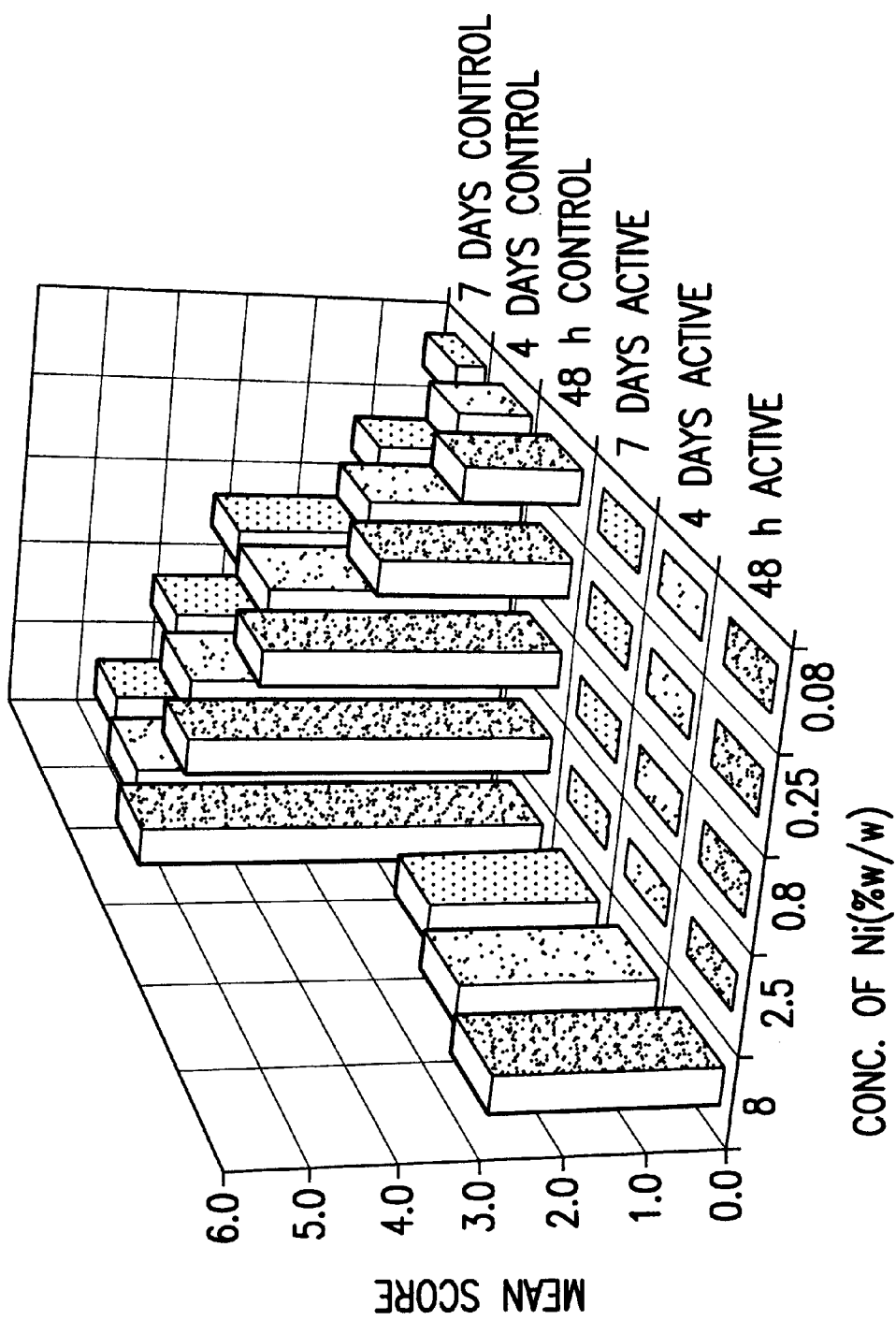
FIG. 4 shows the effect of the active barrier cream after nickel exposure.
Figure 5A:
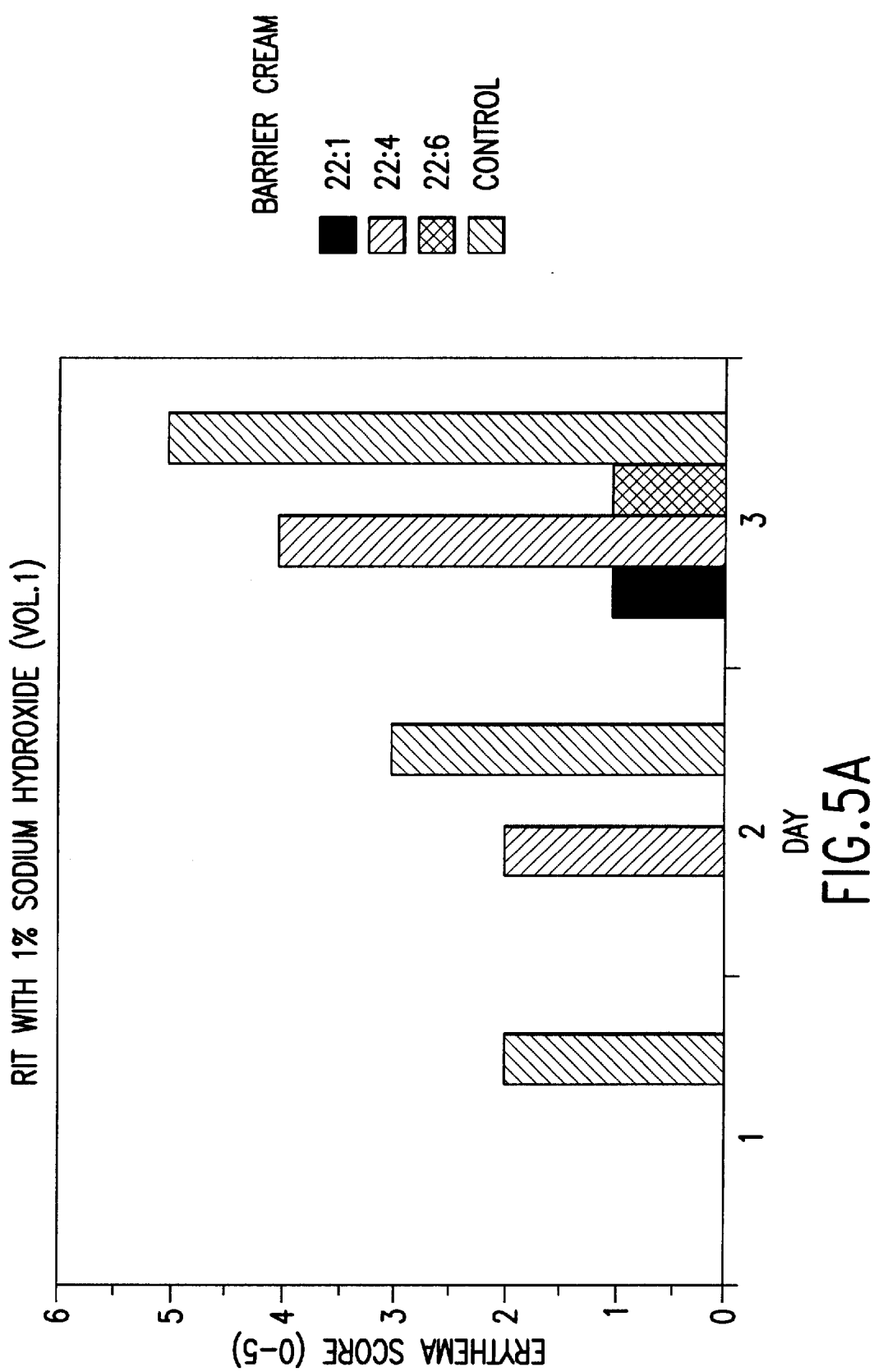
FIGS. 5A and 5B shows the efficacy of skin barrier creams after irritation tests with sodium hydroxide.
Figure 5B:
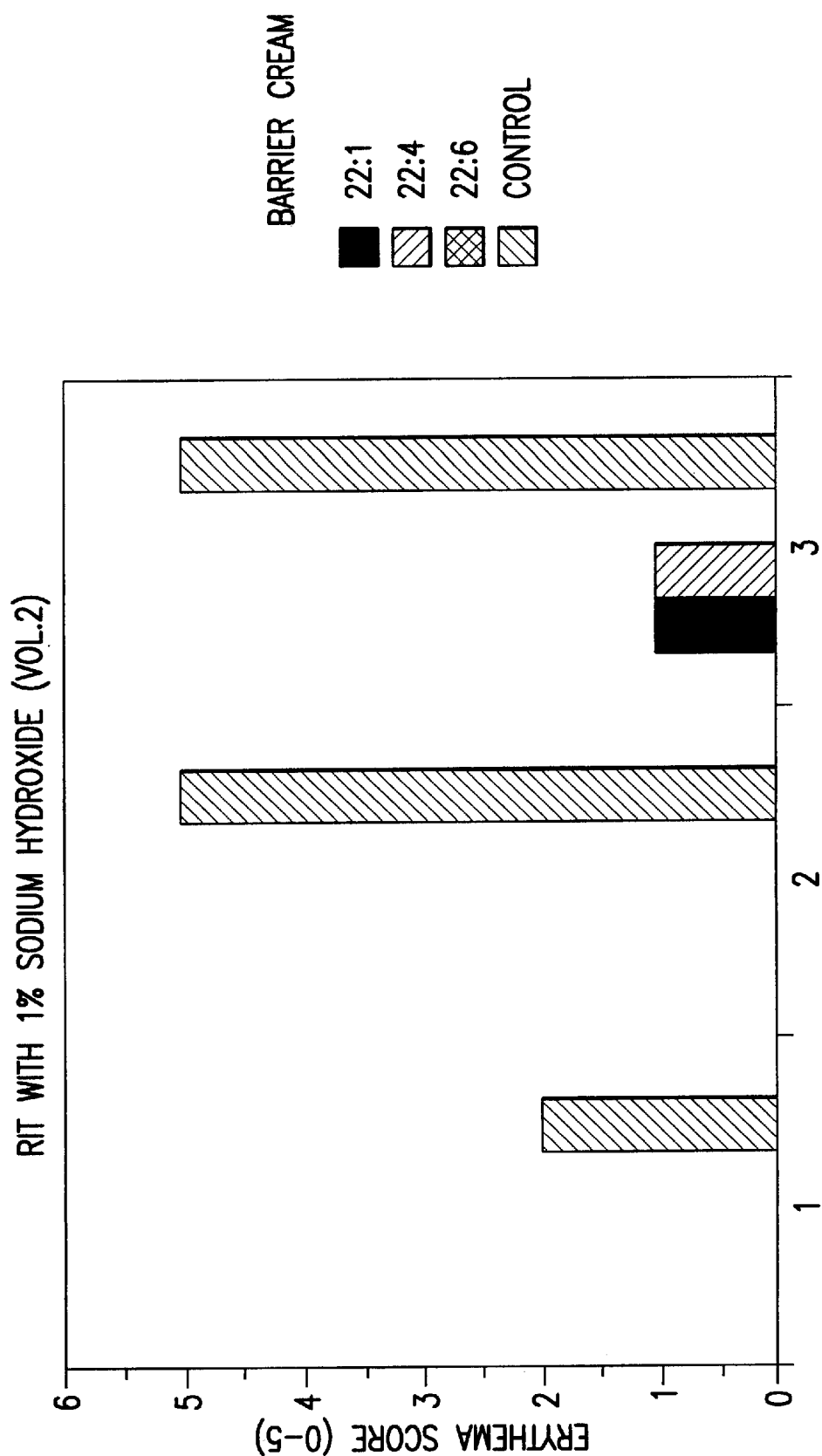

The results are shown in Table 2 and FIG. 5. In Table 2, the results are evaluated at two burden doses of nickel. The two doses were ≧2.5% applied nickel, this concentration is below the maximum binding capacity of the applied chelator; further at a dose of 8% nickel, this dose is higher than the maximum binding capacity of the applied chelator, which is calculated to apply in a dose of approximately 5% nickel. Of the 21 patients examined, 17 patients continued the test during study time. All 17 patients reacted with a significantly positive and almost linear score in relation to the applied doses of nickel (Table 2). The protection against nickel, in 15 out of 17 patients on the test area pretreated with the active gel, was complete at the dose levels ≧2.5% of nickel. Remarkably, three of these patients were also protected against the highest dose of 8% nickel. The protection was even better on the test area pretreated with the active cream. Under these circumstances, 16 out of 17 patients were completely protected against contact to nickel, at nickel doses ≧2.5%. Five of these patients were also unaffected at the highest dose. The 17th patient who reacted to a dose of 2.5% nickel, was, however, unaffected at the lower dose of 0.8% nickel. Moreover, this patient was extremely sensitized to nickel, as shown by maximal scoring at all nickel doses on the blank cream test area. FIG. 4 also shows that the protection against nickel exposure is persistent over time. The column-heights of control exposures are decreasing with time, indicating formation of a stable complex between DTPA and the nickel ions. Apparently, the complex is completely stable and unaffected by biological degradation and metabolism during study time.

During this study, the blank cream was completely dermatologically biocompatible, with no sign of irritation or itching on the skin in any of the patients tested.

TABLE 2

Effect of barrier cream/gel on mean score after Ni exposure for 48 h

|  | Negative | | Positive | |
| --- | --- | --- | --- | --- |
| Applied | ≦2.5% Ni* | 8% Ni** | ≦2.5% Ni* | 8% Ni** |
| Nickelsulphate in water (0.08–8%) | — | — | 17 | 17 |
| Nickelsulphate in water + gel | 15 | 3 | 2 | 14 |
| Nickelsulphate in water + cream | 16 | 5 | 1 | 12 |
| Nickelsulphate in water + blank cream | 0 | 0 | 17 | 17 |

*Ni conc. < max. binding capacity of the chelator
**Ni conc. > max. binding capacity of the chelator

TABLE 2

Results of nickel barrier cream study (Example 1)

| Patient no | Conc (%) of Nickelsulphate | Barrier Gel | Control | Barrier Cream | Blank cream |
| --- | --- | --- | --- | --- | --- |
| 1 | 8 | 2 | 4 | 5 | 5 |
|  | 2.5 | 0 | 2 | 0 | 4 |
|  | 0.8 | 0 | 1 | 0 | 2 |
|  | 0.25 | 0 | 0 | 0 | 1 |
|  | 0.08 | 0 | 0 | 0 | 1 |
| 3 | 8 | 1 | 2 | 2 | 5 |
|  | 2.5 | 0 | 1 | 0 | 4 |
|  | 0.8 | 0 | 2 | 0 | 4 |
|  | 0.25 | 0 | 1 | 0 | 2 |
|  | 0.08 | 0 | 1 | 0 | 2 |
| 5 | 8 | 4 | 5 | 0 | 6 |
|  | 2.5 | 0 | 4 | 0 | 5 |
|  | 0.8 | 0 | 4 | 0 | 5 |
|  | 0.25 | 0 | 1 | 0 | 4 |
|  | 0.08 | 0 | 0 | 0 | 0 |
| 6 | 8 | 4 | 6 | 6 | 5 |
|  | 2.5 | 0 | 6 | 0 | 6 |
|  | 0.8 | 0 | 5 | 0 | 5 |
|  | 0.25 | 0 | 2 | 0 | 3 |
|  | 0.08 | 0 | 0 | 0 | 2 |
| 7 | 8 | 1 | 0 | 0 | 4 |
|  | 2.5 | 0 | 1 | 0 | 6 |
|  | 0.8 | 0 | 0 | 0 | 4 |
|  | 0.25 | 0 | 0 | 0 | 0 |
|  | 0.08 | 0 | 0 | 0 | 1 |
| 8 | 8 | 5 | 5 | 6 | 6 |
|  | 2.5 | 4 | 5 | 5 | 6 |
|  | 0.8 | 0 | 5 | 0 | 6 |
|  | 0.25 | 0 | 4 | 0 | 6 |
|  | 0.08 | 0 | 4 | 0 | 5 |
| 9 | 8 | 0 | 5 | 0 | 6 |
|  | 2.5 | 0 | 4 | 0 | 6 |
|  | 0.8 | 0 | 5 | 0 | 6 |
|  | 0.25 | 0 | 2 | 0 | 2 |
|  | 0.08 | 0 | 1 | 0 | 2 |
| 11 | 8 | 4 | 6 | 4 | 4 |
|  | 2.5 | 4 | 4 | 0 | 4 |
|  | 0.8 | 0 | 6 | 0 | 5 |
|  | 0.25 | 0 | 5 | 0 | 3 |
|  | 0.08 | 0 | 2 | 0 | 0 |
| 12 | 8 | 4 | 5 | 4 | 6 |
|  | 2.5 | 0 | 4 | 0 | 6 |
|  | 0.8 | 0 | 3 | 0 | 5 |
|  | 0.25 | 0 | 2 | 0 | 3 |
|  | 0.08 | 0 | 0 | 0 | 4 |
| 13 | 8 | 1 | 5 | 0 | 6 |
|  | 2.5 | 0 | 4 | 0 | 6 |
|  | 0.8 | 0 | 1 | 0 | 4 |
|  | 0.25 | 0 | 1 | 0 | 3 |
|  | 0.08 | 0 | 1 | 0 | 1 |
| 14 | 8 | 0 | 4 | 6 | 6 |
|  | 2.5 | 0 | 1 | 0 | 4 |
|  | 0.8 | 0 | 1 | 0 | 5 |
|  | 0.25 | 0 | 1 | 0 | 1 |
|  | 0.08 | 0 | 1 | 0 | 2 |
| 15 | 8 | 4 | 6 | 2 | 6 |
|  | 2.5 | 0 | 5 | 0 | 6 |
|  | 0.8 | 0 | 2 | 0 | 4 |
|  | 0.25 | 0 | 2 | 0 | 2 |
|  | 0.08 | 0 | 0 | 0 | 2 |
| 16 | 8 | 2 | 4 | 3 | 4 |
|  | 2.5 | 0 | 1 | 0 | 1 |
|  | 0.8 | 0 | 0 | 0 | 1 |
|  | 0.25 | 0 | 0 | 0 | 1 |
|  | 0.08 | 0 | 0 | 0 | 0 |
| 17 | 8 | 6 | 6 | 3 | 6 |
|  | 2.5 | 0 | 5 | 0 | 6 |
|  | 0.8 | 0 | 3 | 0 | 5 |
|  | 0.25 | 0 | 2 | 0 | 5 |
|  | 0.08 | 0 | 2 | 0 | 2 |
| 18 | 8 | 0 | 3 | 4 | 6 |
|  | 2.5 | 0 | 3 | 0 | 5 |
|  | 0.8 | 0 | 0 | 0 | 4 |
|  | 0.25 | 0 | 0 | 0 | 4 |
|  | 0.08 | 0 | 0 | 0 | 2 |
| 19 | 8 | 3 | 4 | 0 | 6 |
|  | 2.5 | 0 | 3 | 0 | 3 |
|  | 0.8 | 0 | 0 | 0 | 1 |
|  | 0.25 | 0 | 0 | 0 | 1 |
|  | 0.08 | 0 | 0 | 0 | 0 |
| 20 | 8 | 5 | 6 | 3 | 6 |
|  | 2.5 | 0 | 3 | 0 | 6 |
|  | 0.8 | 0 | 3 | 0 | 3 |
|  | 0.25 | 0 | 2 | 0 | 3 |
|  | 0.08 | 0 | 4 | 0 | 1 |
| Total score |  | 54 | 214 | 53 | 317 |
| Mean score |  | 3.17 | 12.59 | 3.12 | 18.65 |

SCORE: (+) = 1, + = 2, +(+) = 3, ++ = 4, ++(+) = 5, +++ = 6

In conclusion, the test formulation of this active barrier composition has extremely high protective efficiency against nickel, in patients with a clinical diagnosis of nickel contact dermatitis.

Example 1b

A w/o Cream-Based Active Barrier Formulation Intended for Protection Against Nickel Exposition 75 g DTPA and 23 g sodium hydroxide are dissolved in 657 g purified water and 30 g 85% glycerol. 25 g chitosan hydrochloride is dissolved in the DTPA solution (pH=5–6). This solution is added to 90 g paraffin liquid, 60 g isohexadecan and 40 g polyoxypropylenepolyoxyethylene glycerol sorbitan hydroxyisostearate. The mixture is homogenised until a creamy consistency appears. A preservative (e.g. sorbic acid) may also be added. Creams containing low amounts of DTPA has to be stabilised by a salt (e.g. magnesium chloride).

Example 1c
A o/w Cream-Based Active Barrier Formulation Intended for Protection Against Nickel Exposition 75 g DTPA and 23 g sodium hydroxide are dissolved in 702 g purified water and 15 g 85% glycerol. 25 g chitosan hydrochloride is dissolved in the DTPA solution (pH 5–6). 15 g polyoxyethylene-2-stearylether, 10 g polyoxyethylene-21-stearylether, 50 g paraffin liquid, 50 g polyoxypropylene-15-stearyl alcohol and 35 g cetostearyl alcohol are mixed and melted together at 70° C. The DTPA solution is heated to 70° C. and mixed with the hydrophobic ingredients (70° C.). The mixture is cooled to 40–45° C. during homogenisation. During stirring the cream is cooled to below 30° C. A preservative (e.g. sorbic acid and/or phenoxyethanol) may also be added.

Example 2
A Cream-Based (Active) Barrier Formulation Intended for Protection Against Irritative, Corrosive, Dissolving and Intoxicating Agents The formulation is based on ingredients similar to those described in Example 1. However, the antiallergen, DTPA, can be excluded or exchanged for other antiallergens, depending on the intended use of this formulation. If the harmful agents are chemically reactive, the formulation can be supplied with e.g. a scavenger substance, e.g. taurine, hypotaurine, cysteamine, or by addition of activated chitosan.

1.0 g taurine and 4.0 g urea are dissolved in 69.15 ml physiological saline (pH 6.5). 1.85 g chitosan carbamate (Mw: approximately 180 kd) is dissolved in the physiological saline solution, 4.0 ml of 1.0 mol/l hydrochloric acid is added, and the solution is mixed until the polymer is completely dissolved. 12 g cetylstearyl alcohol, 5 g polyoxyethylene-2-sterarylether, 1.5 g glycerol and 1.5 g paraffine liquid are mixed and melted together in a water bath at 70–75° C. The gel solution is heated to 60° C. and mixed with the hydrophobic ingredients at 60° C. until a creamy consistency appears. An authorized preservative may also be added.

Figure 7A:
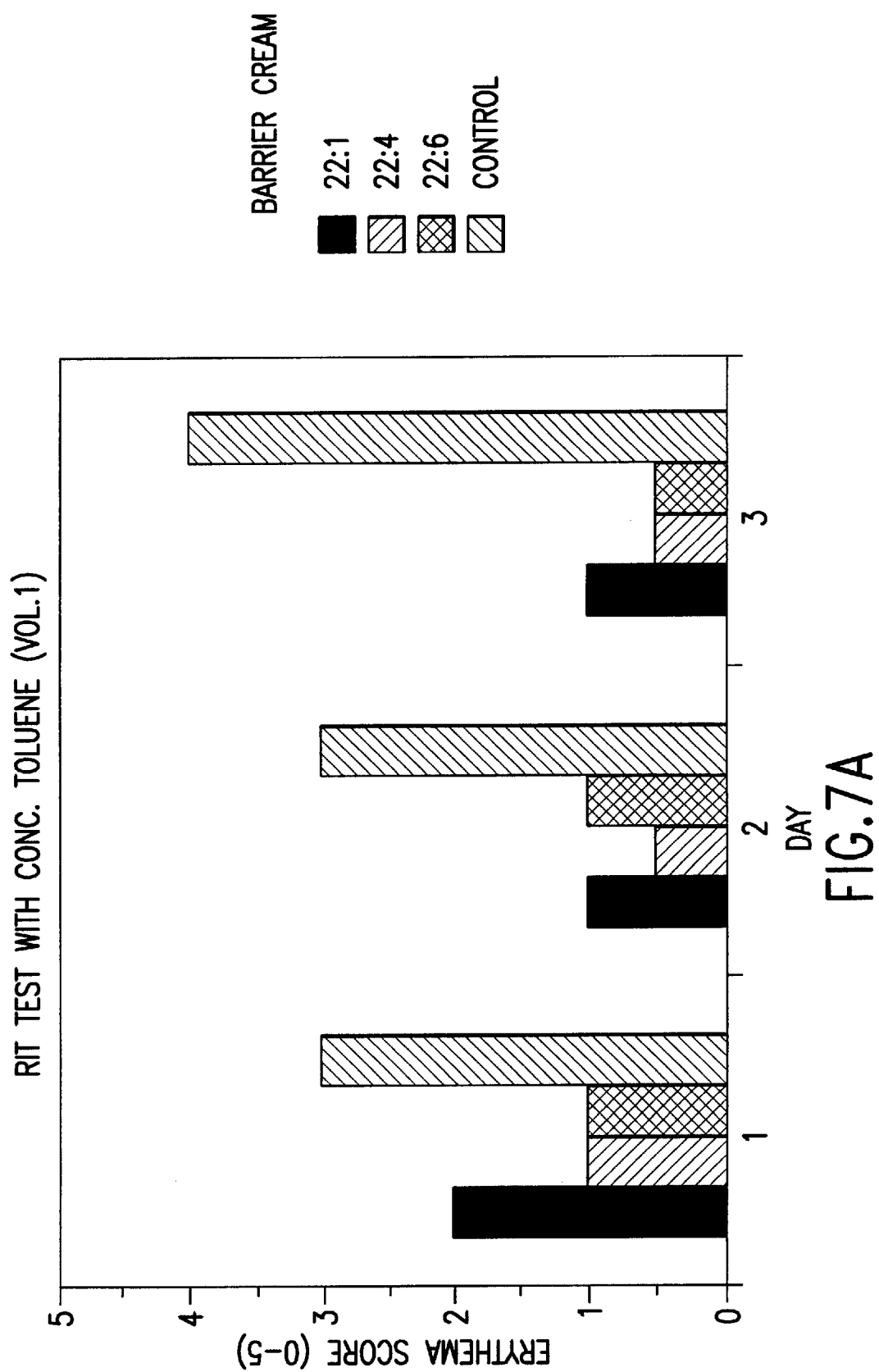
FIG. 7 shows the efficacy of skin barrier creams after irritation tests with toluene.
Figure 7B:
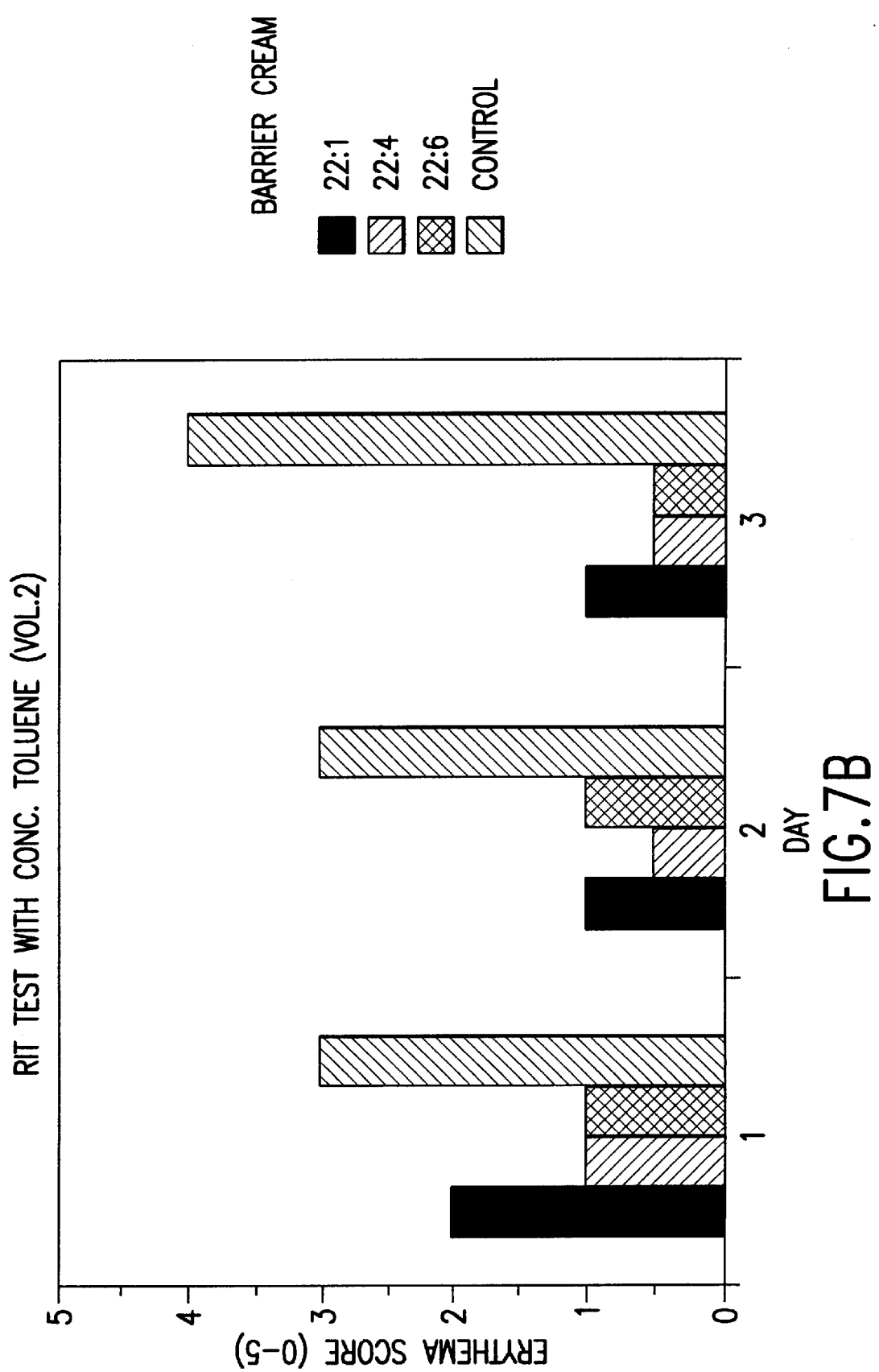

Cutaneous irritation was tested by the repetitive irritation test (RIT) method proposed by Frosch (Cont. Derm. 29: 1993: 113–118) in two human volunteers. Three protective formulations were investigated, and the basic compositions agreed with the formulation described in example 2 (22:6=F1). In the first of the additional formulations, taurine was excluded (22:4=F2), and in the second, taurine and chitosan carbamate, and replaced by native chitosan (22:1=F3). The test area was the paravertebral skin on the midback, with four separate test fields. The fields were randomized for each formulation, and treated with 0.35 ml of the formulation decided, on a skin area of 33 cm². One area served as an untreated control. The RIT was performed with four standard irritants, 10% sodium lauryl sulphate (SLS), 1.0% sodium hydroxide (NaOH), 30% lactic acid (LA) and undiluted toluene (Tol). The irritants were applied after 30 minutes in IQ chambers (81 mm²), containing 40 µl of the detergent, base and acid, and 30 µl of the organic solvent. The chambers were removed after 30 minutes of exposure, and the skin was cleaned with soft paper tissue. Using this scheme of application repeatedly, volunteers were treated on three consecutive days. The erythema score was followed daily by visual scoring on a scale, 0–5 (0=no reaction; 5 very severe epidermal effects). The results are shown in FIGS. 5–7. The results of SLS irritation (not shown in the figures) showed a complete protection during all five days for all formulations, compared with the untreated sites. FIG. 6 shows the result for NaOH, and the less protective effect compared to SLS irritation. The highest efficacy was observed for F1 with almost complete protection for three days. From control fields, the maximal erythema score was reached on day number two in one volunteer and on day number three in the other. The result obtained by LA is shown in FIG. 7.

Figure 8:
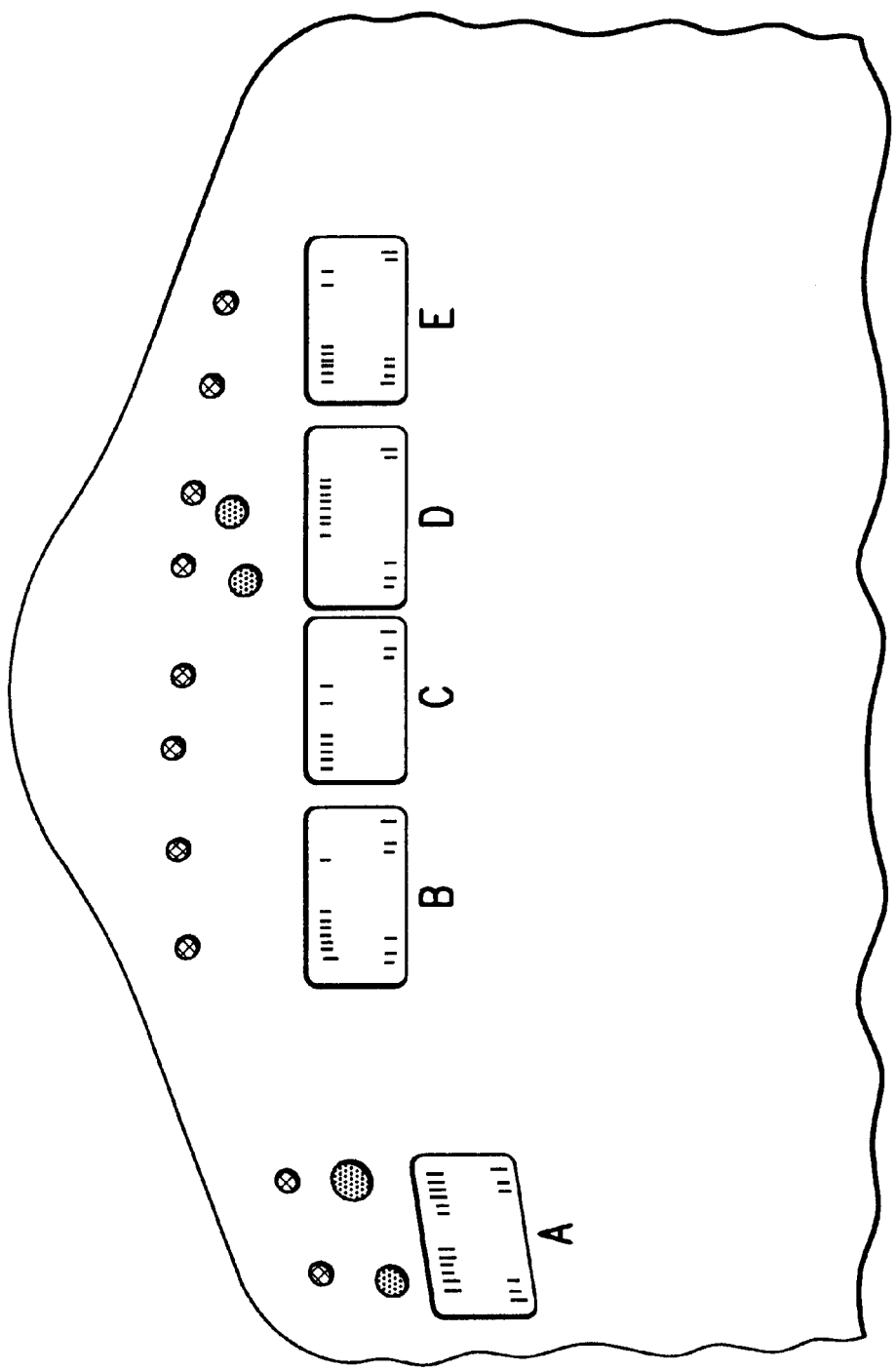
FIG. 8 shows the UV sequestration capacity of polyethylene-N-PABA and EHD-PAVA applied in a cream on human skin.

Treatment with all three formulations gave a complete protection against the LA burden. None of the formulations showed complete protection against Tol (FIG. 8). However, the skin irritation was less after treatment with F1 and F2, and there was a tendency of a progressive protection by particularly F1, indicating that maximal protection might be obtained against irritation caused by action of organic solvents, after repeated administration of formulation 1.

Example 3
A Cream-Based Active Formulation Intended for Protection Against Sesquiterpene Lactones (Plant Allergen)

2.0 g urea is dissolved in 7.1 ml physiological saline (pH 6.5). 0.5 g chitosan chloride (Mw: approximately 50 kd) is dissolved in the physiological saline solution and mixed until the polymer is completely dissolved. 1.2 g cetylstearylalcohol, 0.5 g polyoxyethylene-2-sterarylether, 0.2 g glycerol and 0.1 g paraffine liquid are mixed and melted together in a water bath at 70–75° C. The gel solution is heated to 60° C. and mixed with the hydrophobic ingredients at 60° C. until a creamy consistency appears. An authorized preservative may also be added.

A patient with clinically verified contact hypersensitivity against sesquiterpene lactones was treated with 0.1 ml of the chitosan chloride based formulation, on a 9 cm² skin area on the right mid-back. After 30 min the patient was patch-tested using three IQ chambers, containing 15 mg of sesquiterpene lactone mix (0.1% pet. Mx-18; Chemotechnique Diagnostics, Malmö, Sweden). One patch-test was applied over the treated area, the second on an untreated skin 10 cm below the test field. The third test was applied on the left mid-back, also on an untreated skin area. The patient was exposed for 12 hours. Evaluation of the test result was performed by visual scoring, on a scale (0, ±,+, ++, ++±, +++) at 24 and 48 hours and 7 days after treatment.

The result is shown in Table 3.

TABLE 3

Protection by chitosan chloride against sesquiterpene lactones

| | Scoring | | |
| --- | --- | --- | --- |
| | 24 h | 48 h | 7 days |
| Test area right mid-back | 0 | 0 | 0 |
| Control area right mid-back | ± | + | 0 |
| Control area left mid-back | +++ | +++ | ++± |

The result shows that chitosan chloride is a very effective barrier against sesquiterpene lactones under the conditions of in vivo patch testing. A complete protection is observed on all scoring days.

Example 4
A Cream-Based Active Formulation Intended for Protection Against Harmful UV B Radiation 0.5 g and 1.0 g each of PE-N-aminobenzoic acid (P-PABA) (Mw: approximately 60 kdal) was dissolved in two separate vials each containing 2 ml ethanol. Most of the ethanol was evaporated until a viscous residue remained. Petrolatum was added to give a final concentration of 5% and 10% (w/w) in the formulation, respectively. The formulation was mixed in a water bath at 70–75° C.

The biological light protection factor of the sunscreen formulation was determined at two concentrations of the active agent, P-PABA. The two formulations were prepared and tested at a concentration of 5.0% and 10% (w/w). For comparison, one control sunscreen agent was also studied. The UV B protection agent, ethylhexyl-4-dimethylaminobenzoic acid (EHD-PABA) was prepared at a concentration of 5.0% (w/w) in petrolatum. The test was performed on the skin of two volunteers, under standardized conditions by application of 0.1 ml of the formulation per 100 $cm^2$ of skin area on their backs.

An Osram Ultravitalux lamp was used as light source. The light protection factor was determined and compared to vehicle and untreated skin after light exposure on cylindrical (1.0 cm i.d.) skin areas for 16 and 32 seconds. The results were evaluated from intensity of the erythema score (FIG. 8; A) untreated control, b) 10% P-PABA, c) 5% P-PABA, D) vehicle, and E) EHD-PABA. Light exposure as indicated on each skin area for 16 seconds (left) and 32 seconds (right)). The biological protection against UV B radiation obtained by the UV B standard EHD-PABA absorber was almost similar to the protection by the polymeric P-PABA derivative. Added at the low (5.0% (w/w)) concentration, the protection by P-PABA was complete at light exposure for 16 and 32 seconds, while the protection by EHD-PABA was insufficient at 32 seconds in one of the volunteers. The result indicates that soluble UV B absorbers can be replaced by polymeric UV B sequestrating compounds with sustained UV B quenching capacity.

Example 5
A Cream-Based Active Formulation Intended for Treatment of Herpes Simplex Infections and Tinea Dermatomycoses 2.0 g urea is dissolved in 37.0 ml physiological saline (pH 6.5). 1.25 g chitosan carbamate (Mw: approximately 180 kd) is dissolved in the physiological saline solution and mixed until the polymer is completely dissolved. 6.0 g cetylstearylalcohol, 2.5 g polyoxyethylene-2-sterarylether, 1.0 g glycerol and 0.5 g paraffine liquid are mixed and melted together in a water bath at 70–75° C. The gel solution is heated to 60° C. and mixed with the hydrophobic ingredients at 60° C. until a creamy consistency appears. An authorized preservative may also be added.

In pilot studies, three subjects with regular Herpes simplex infections and two subjects with severe Tinea mycoses on both feet were treated by topical application of the chitosan carbamate formulation. For successful treatment of the Herpes simplex virus infection, it is imperative to start the treatment as early as possible, preferably in the prodromal phase of the infection by application of the formulation on an expanded skin area around the infected tissue. Treatment may be repeated several times during the first day of infection, to ensure a complete cover of the infected skin area. Advanced infection with initiated tissue necroses can not be treated successfully. The result from single and repeated treatment(s) of skin lesions, indicate that immediate medication of infected tissue is imperative for complete inhibition of the viral replication phase. A delay in the start of treatment for one or two hours results in a normal progressive infection.

The Tinea infection may be treated by application of the formulation on the skin, so that it completely covers the affected skin area, twice a day, in the morning and in the evening, by rubbing the cream into the skin. The treatment must be applied continuously for at least seven to ten days, or until the infection ceases, usually within the first week of treatment. Relapse may be treated efficiently by a short-term repeated regimen.

The compositions in Example 1 also exhibit good effects in the treatment of Herpes simplex in some treated subjects.

Example 6
A Cream-Based Active Formulation Intended for Treatment of Chronical Psoriatric Plaques The formulation in Example 2 was used in a pilot study. One subject with plaque-type psoriasis vulgaris on arms and lower extremities was studied. The patient had been free of other topical antipsoriatic medication for at least two weeks. The patient was subject to self-medication. In the treated skin areas affected by the disease, a complete clearing or improvement was achieved, when evaluated after seven days of treatment. The subject experienced a less hyperproliferative scaling of the skin and a ceasing inflammation.

References
1. Menné T. The prevalence of nickel allergy among women. Dermatosen in Beruf und Umwelt 26:123, 1978.
2. Peltonen L. Nickel sensitivity in the general population. Contact Dermatitis 5:27, 1979.
3. Prystovsky S. D., et al. Allergic contact hypersensitivity to nickel, neomycin, ethylenediamine and benzocaine. Arch Dermatol: 115:959, 1979.
4. Maibach H. I. & MenneT. Nickel and the skin: Immunology and Toxicology. Chapter 13:134, 1989, CRC Press, Florida, USA.
5. Menné T, Bachmann E. Permanent disability from hand dermatitis in females sensitive to nickel, chromium and cobalt. Dermatosen in Beruf und Umwelt 27:129, 1979.
6. Menné T., Borgan Ö., Green A. Nickel allergy and hand dermatitis in a stratified sample of the Danish female population: an epidemiological study including a statistic appendix. Acta Dermatovener 62:35, 1982.
7. Emmett E. A. et al. Allergic contact dermatitis to nickel. Bioavailability from consumer products and provocation threshold. J Am Acad Dermatol 19:314, 1988.
8. Christensen J. D. Disulfiram treatment of three patients with nickel dermatitis. Contact Dermatitis 8:105, 1982.
9. Burrows D. et al. Treatment of nickel dermatitis with Trientine. Contact Dermatitis 15:55, 1986.
10. Gawkrodger D. J. et al. The prevention of nickel contact dermatitis. Contact Dermatitis 32:257, 1995.
11. Memon A. A. et al. the inhibitory effects of topical chelating agents and antioxidants on nickel-induced hypersensitivity reactions. J Am Acad Dermatol 30:560, 1994.
12. Van Ketel W. G., Bruynzeel D. P. Chelating effect of EDTA on nickel. Contact Dermatitis 11:311, 1984.
13. Fullerton A, MenneT. In vitro and in vivo evaluation of the effect of barrier gels in nickel contact allergy. Contact Dermatitis 32:100, 1995.
14. Resl.(SR) V, Sykora J. Resl Jr. Effectiveness of tin chelates of EDTA, CDTA, and DTPA in the detoxification of chromium, nickel and cobalt compounds and their application in dermatology. Cs Dermatologie 50:95, 1975.
15. Sjövall P., Christensen O. B., Möller H. Oral hyposensitization in nickel allergy. J Am Acad Dermatol 17:774, 1987.
16. Kligman A. Hyposensitization against Rhus dermatitis. Arch Dermatol 78:47, 1958.
17. Epstein W. L., et al. Induction of antigen specific hyposensitization to poison oak in sensitized adults. Arch Dermatol 118:630, 1982.
18. Frosch P. J. and Kurte A. Efficacy of skin barrier creams. Contact Dermatitis 31:161, 1994.

What is claimed is:
1. A composition for use as a medicament in a topical barrier formulation, an UV radiation absorbing formulation, and an antiviral, antifungal, or anti-inflammatory formulation, comprising:
a cationic, hydrophilic, amine containing polymer, selected from the group consisting of cationic derivatives of native chitosan;
bound to an anionic scavenger substance, which is either
  a) selected from the group consisting of anionic ethylene amine compounds, tetraazacycloalkane-N,N,N,N-tetraacetic acids; and polymer derivatives of porphyrines, or,
  b) in the case of use in an UV radiation absorbing formulation, an antiviral, antifungal or anti-inflammatory formulation, an endogenous compound,
with the proviso that cationic derivatives of native chitosan are not covalently bound to diethylenediaminepentaacetic acid (DTPA) or ethylenediaminetetraacetic acid (EDTA),
with the further proviso that when a cationic derivative of native chitosan and EDTA are present, the amount of EDTA exceeds 0.5 weight percent, and
with the further proviso that when a cationic derivative of native chitosan is present, taurine and taurine derivatives are not present.

2. The composition according to claim 1, wherein the native chitosan has a molecular weight of 1–1000 kdal.

3. The composition according to claim 2, wherein the native chitosan has a molecular weight of 50–250 kdal.

4. The composition according to claim 1, wherein the anionic ethylene amine compounds are selected from the group consisting of DTPA and calcium and sodium salts thereof, EDTA, triethylenetrianiinehexaacetic acid, ethylenediaminetetra-(methyiphosphoric acid), diethylenetriaminepenta-(methylphosphoric acid) (DTPMPA) and homologs thereof, and tetraethylenetetraaminehexaacetic acid the tetraazacycloalkane-N,N,N,N-tetraacetic acids are selected from the group consisting of 1,4,7,10-tetraazacyclo-dodecanetetraacetic acid (DOTA), 1,4,7,10-tetraazacyclotridecanetetra-acetic acid (TRITA), and 1,4,8,11-tetraazacyclotetradecanetetraacetic acid (TETA); the polymer derivatives of porphyrines are tetra(4-carboxyphenyl)-porphyrine; and the endogenous compound is chosen from the group consisting of taurine, hypotaurine, and chlorinated or carbamylated derivatives thereof, cysteanilne, cysteine, N-acetylcysteine, and acidic metabolites of polyamines.

5. The composition according to claim 1, wherein the composition is used in a topical barrier formulation for protection against dermatological disorders induced by inorganic and organic allergens and/or skin irritating agents by binding allergens and/or irritating agents selected from the group consisting of:
  a) $Ni^{2+}$, $Ci^{3+}$, $Cr^{6+}$, $Co^{2+}$, $Au^+$ and $Au^{3+}$;
  b) sesquiterpene lactones, urushiol, latex, epoxy, and acrylate compounds; and
  c) detergents, alkaline products, acidic products, and solvents, wherein the cationic, hydrophilic polymer is ionically bound to the anionic scavenger substance.

6. The composition according to claim 5, wherein the topical barrier formulation is a cream, an ointment, a gel, or an oil.

7. The composition according to claim 1 for use in a protective UV A and UV B radiation absorbing formulation, wherein the cationic, hydrophilic amine containing polymer, is cationic derivatives of native chitosan, and is covalently bound to the scavenger substance, which is chosen from the group consisting of DTPA, triethylenetriaminehexaacetic acid, ethylenediaminetetra-(methyiphosphoric acid), DTPMIPA, and homologs thereof, wherein the scavenger substance, which is covalently bound to the polymer, is complexed with $Cu^{2+}$, $Fe^{2+}$, $Fe^{3+}$ or $Eu^{3+}$ ions or combinations thereof, optionally via an inimobilizable spacer,
with the proviso that cationic derivatives of native chitosan are not covalently bound to DTPA or EDTA.

8. The composition according to claim 7, wherein the UV A and UV B radiation absorbing formulation is a cream, an ointment, a gel, a liniment, a lotion, an oil, or a lip preparation.

9. The composition according to claim 1, which comprises:
about 0.05–15 percent by weight, based on a total weight of the composition, of the cationic, hydrophilic amine containing polymer, and
about 0.5–20 percent by weight, based on the total weight of the composition, of the anionic scavenger substance.

10. The composition according to claim 1, which further comprises a lipophilic substance and, optionally, one or more additives chosen from the group consisting of an emulsifier, a surfactant, an emollient, a preservative, a humectant, an antioxidant, and a fragrance.

11. A process of making a protective and/or therapeutic topical barrier formulation comprising combining a composition according to claim 5 with a suitable carrier to form said formulation.

12. A process of making an UV radiation absorbing formulation for prevention of dermatological disorders induced by UV A and UV B radiation comprising: combining a composition according to claim 7 with a suitable carrier to form said formulation.

13. The composition according to claim 1, which comprises:
about 0.05–15 percent by weight, based on a total weight of the composition, of the cationic, hydrophilic amine containing polymer, and
about 5–15 percent by weight, based on the total weight of the composition, of the anionic scavenger substance.

14. The composition according to claim 1, which comprises:
about 0.5–5.0 percent by weight, based on a total weight of the composition, of the cationic, hydrophilic amine containing polymer, and
about 0.5–20 percent by weight, based on the total weight of the composition, of the anionic scavenger substance.

15. The composition according to claim 1, which comprises:
about 0.5–5.0 percent by weight, based on a total weight of the composition, of the cationic, hydrophilic amine containing polymer, and
about 5–15 percent by weight, based on the total weight of the composition, of the anionic scavenger substance.

16. The composition according to claim 5, wherein the cationic, hydrophilic polymer is cationic derivatives of native chitosan, and the anionic scavenger substance is DTPA.

17. The composition according to claim 7 for use in a protective UV A and UV B radiation absorbing formulation, wherein the scavenger substance is DTPA with the proviso that cationic derivatives of native chitosan are not covalently bound to the DTPA.

18. A composition for use as a medicament in a topical barrier formulation, an UV radiation absorbing formulation, and an antiviral, antifungal, or anti-inflammatory formulation, comprising:
- a cationic, hydrophilic, amine containing polymer, selected from the group consisting of cationic derivatives of native chitosan;
- bound to an anionic scavenger substance, which is either
  - a) selected from the group consisting of anionic ethylene amine compounds, tetraazacycloalkane-N,N,N,N-tetraacetic acids; and polymer derivatives of porphyrines, or,
  - b) in the case of use in an UV radiation absorbing formulation, an antiviral, antifungal or anti-inflammatory formulation, an endogenous compound, wherein
- said scavenger substance binds or entraps inorganic allergens, organic allergens, and skin irritating agents once applied as a topical barrier,
- with the proviso that cationic derivatives of native chitosan are not covalently bound to diethylenediaminepentaacetic acid (DTPA) or ethylenediaminetetraacetic acid (EDTA),
- with the further proviso that when a cationic derivative of native chitosan and EDTA are present, the amount of EDTA exceeds 0.5 weight percent, and
- with the further proviso that when a cationic derivative of native chitosan is present, taurine and taurine derivatives are not present.

* * * * *